United States Patent [19]

Acher et al.

[11] Patent Number: 4,835,172

[45] Date of Patent: May 30, 1989

[54] NOVEL BENZAMIDES, INTERMEDIATES AND PROCESS FOR THE PREPARATION AND THERAPEUTIC USE THEREOF

[75] Inventors: Jacques Acher, Itteville; Jean-Claude Monier, Lardy; Jean-Paul Schmitt, Arpajon; Reneè Gardaix-Luthereau, Cachan; Brenda Costall; Robert Naylor, both of Addingham, all of France

[73] Assignee: Societe D'Etudes Scientifiques et Industrielles de L'Ile-de-France, Paris, France

[21] Appl. No.: 943,708

[22] Filed: Dec. 19, 1986

[30] Foreign Application Priority Data

Dec. 19, 1985 [FR] France ................ 85 18829

[51] Int. Cl.$^4$ ............ C07D 235/50; C07D 277/18; C07D 263/30; A01N 43/50
[52] U.S. Cl. .................... 514/392; 548/315; 548/194; 548/234; 558/17; 560/35; 560/43; 564/26
[58] Field of Search ............ 548/315; 514/392

[56] References Cited

U.S. PATENT DOCUMENTS

| | | | |
|---|---|---|---|
| 3,342,826 | 9/1967 | Miller et al. | 260/294 |
| 3,682,968 | 8/1972 | Shon | 564/617 |
| 4,461,904 | 7/1984 | York | 548/315 |

FOREIGN PATENT DOCUMENTS

| | | | |
|---|---|---|---|
| 81924 | 6/1983 | European Pat. Off. | 348/315 |
| 2905883 | 8/1980 | Fed. Rep. of Germany | 548/315 |
| 1539104 | 9/1968 | France | 564/167 |

Primary Examiner—Robert Gerstl

Attorney, Agent, or Firm—Fitzpatrick, Cella, Harper & Scinto

[57] ABSTRACT

New substituted benzamides have the general formula:

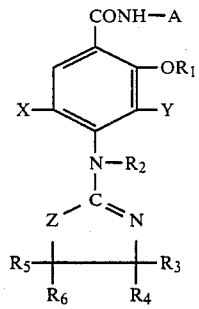

A=alkyl, alkenyl, diethylaminoethyl or

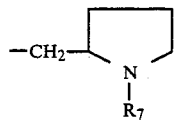

$R_1$, $R_2$=H, $C_1$–$C_6$ alkyl, $C_2$–$C_6$ alkenyl;
$R_3$, $R_4$, $R_5$, $R_6$=hydrogen or $C_1$–$C_6$ alkyl;
X=halogen;
Y=H, halogen;
Z=NH, oxygen or sulfur;

their optical isomers and their physiologically acceptable salts. The compounds are used as activators of the central nervous system.

14 Claims, 7 Drawing Sheets

COMPOUND: EXAMPLE 1

COMPOUND: EXAMPLE 4

COMPOUND:
EXAMPLE 5

COMPOUND:
EXAMPLE 2

COMPOUND:
EXAMPLE 9

COMPOUND:
EXAMPLE 16

COMPOUND:
EXAMPLE 15

COMPOUND:
EXAMPLE 14

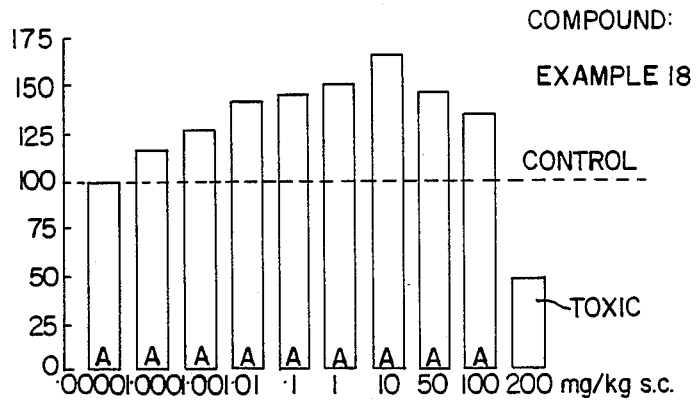
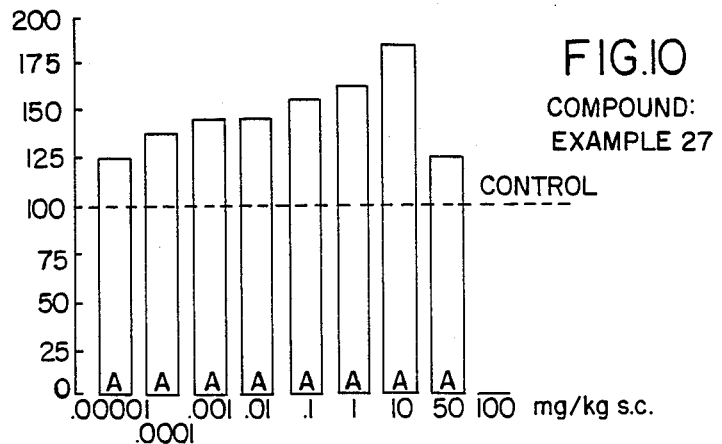

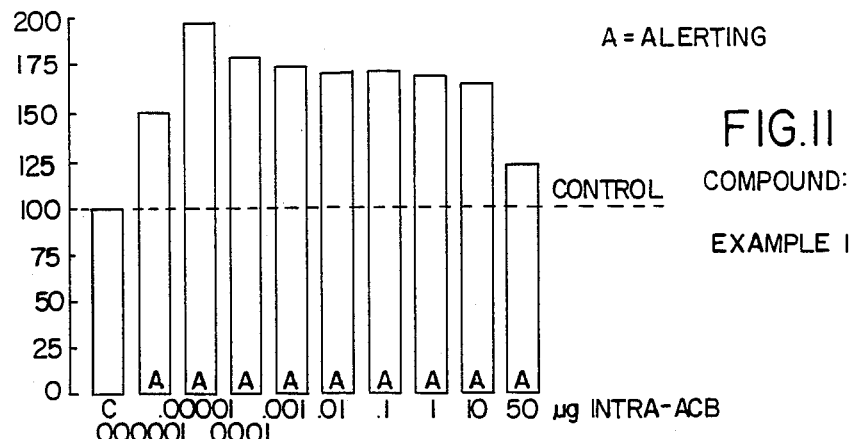
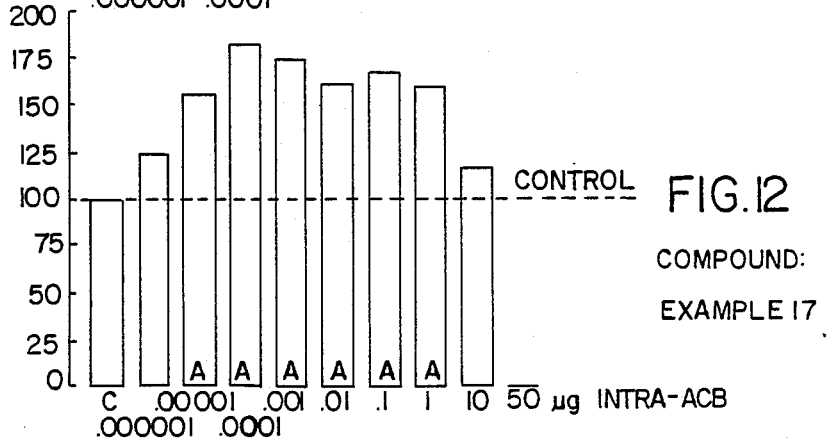
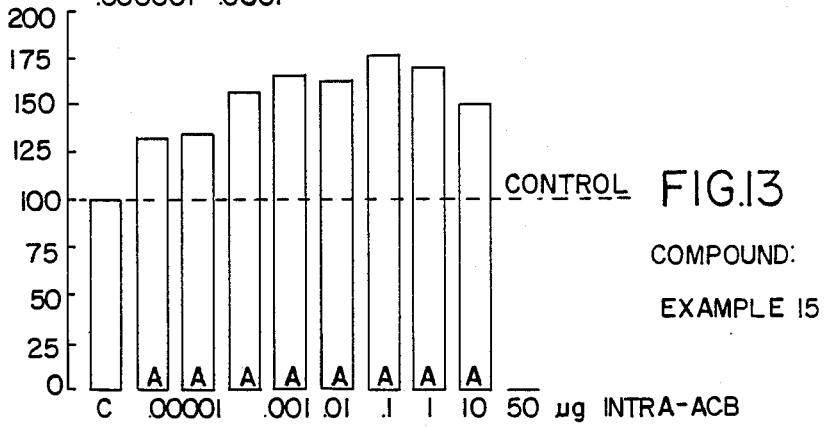

NOVEL BENZAMIDES, INTERMEDIATES AND PROCESS FOR THE PREPARATION AND THERAPEUTIC USE THEREOF

The invention relates novel substituted benzamides and their physiologically acceptable salts, corresponding to the following general formula (I):

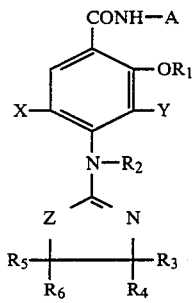

A represents $C_1$–$C_6$ alkyl, $C_2$–$C_6$ alkenyl, diethylaminoethyl, or a group of the formula:

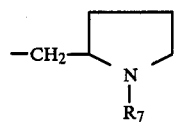

$R_7$ is hydrogen, $C_1$–$C_6$ alkyl, $C_2$–$C_6$ alkenyl, aryl, aryl-substituted $C_1$–$C_6$ alkyl, $C_3$–$C_6$ cycloalkyl, $C_3$–$C_6$ cycloalkyl substituted $C_1$–$C_6$ alkyl, $C_4$–$C_6$ cycloalkenyl or $C_4$–$C_6$ cycloalkenyl substituted $C_1$–$C_6$ alkyl, $R_1$ and $R_2$ each represent a hydrogen atom, $C_1$–$C_6$ alkyl or $C_2$–$C_6$ alkenyl, $R_3$, $R_4$, $R_5$ and $R_6$ each represent a hydrogen atom or $C_1$–$C_6$ alkyl, X is a halogen atom, preferably a chlorine or bromine, Y is a hydrogen atom or a halogen, preferably a chlorine or bromine, and —Z is a NH group or an oxygen or sulphur atom, Each of the alkyl and alkenyl residues of formula I, whether cyclic or acyclic, contain a maximum of 6 carbon atoms, The invention also relates to the methods of preparing these compounds, including intermediates and medicaments containing these benzamides.

Pharmacologically acceptable salts of formula I compounds include the non-toxic acid addition salts formed by reacting the benzamides of the invention with the desired acid. The acid may be an inorganic acid, such as sulfuric, sulfamic, nitric, hydrobromic, hydrochloric, phosphoric and the like, or an organic acid, such as citric, tartaric, lactic, acetic, succinic, fumaric, maleic, benzoic and the like.

Pharmacologically acceptable salts of formula I compounds also include the non-toxic quaternary ammonium salts of the benzamides of the invention produced by reacting the benzamides with an aliphatic or aromatic alkylating agent, such as methyl chloride, methyl bromide, dimethyl sulfate, methyl p-toluene sulfonate and the like. In addition, the novel benzamide compounds include the N-oxides formed by utilizing the conventional agents; see, for example, U.S. Pat. No. 3,839,330, issued Oct. 1, 1974.

When the presence of an asymmetric carbon atom in the formula makes it possible to have optical isomers these also form part of the invention.

The dextrorotatory and levorotatory isomers of the foregoing compounds of the invention are also included within the scope of this invention. Such optically active compounds are conventionally resolved employing a suitably selected optically active acid, which is added to the racemate. The salts thus obtained are separated, for example, by making use of their differences in solubility in an appropriate solvent or by other conventional techniques. Typically, D- or L-dibenzoyl-tartaric acid is employed to resolve the racemate.

The compounds have therapeutic uses, particularly in activating the central nervous system.

Preferred benzamides correspond to formula (IA):

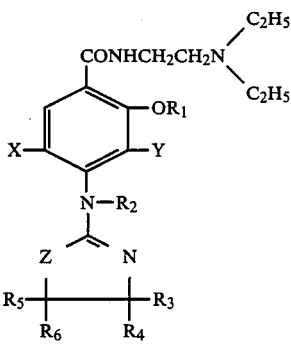

wherein $R_1$, $R_2$, $R_3$, $R_4$, $R_5$, $R_6$, X, Y and Z each have the same meaning as set forth in formula I above. More preferred benzamides within the scope of this invention and formula IA include the following:

(i) N-[2-(diethylamino)ethyl]2-methoxy 4-[(1-H 4,5-dihydro 2-imidazolyl)amino]5-chloro benzamide;

(ii) N-[2-(diethylamino)ethyl]2-methoxy 4-[N-ethyl, N-(1-H 4,5-dihydro 2-imidazolyl)amino]5-chloro benzamide;

(iii) N-[2-(diethylamino)ethyl]2-methoxy 3,5-dichloro 4-[(1-H 4,5-dihydro 2-imidazolyl)amino]benzamide;

(iv) N-[2-(diethylamino)ethyl]2-methoxy 4-[(1-H 4,5-dihydro 4-dimethyl 2-imidazolyl)amino]5-chloro benzamide;

(v) N-[2(diethylamino)ethyl]2-methoxy 4-[(4,5-dihydro, 1,3-thiazol 2-yl)amino]5-chloro benzamide; and (vi) N-[2(diethylamino)ethyl]2-methoxy 4-[(4,5-dihydro 2-oxazolyl) amino]5-chloro benzamide.

Additional preferred benzamides of this invention correspond to formula (IB):

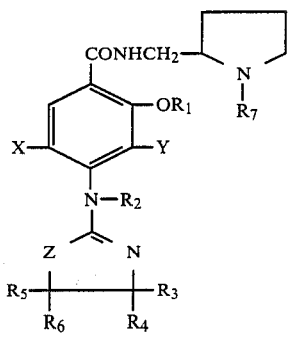

wherein $R_1$ through $R_7$, X, Y and Z each have the same meaning as set forth in formula 1 above.

More preferred benzamides within the scope of this invention and formula 1B include the following:

(i) N-[(1-ethyl 2-pyrrolidinyl)methyl]2-methoxy 3,5-dibromo 4-[(1-H 4,5-dihydro 2-imidazolyl)amino] benzamide;

(ii) N-1[(1-cyclohexenylmethyl 2-pyrrolidinyl)methyl]2-methoxy 4-[(1-H 4,5-dihydro 2-imidazolyl amino]5-chloro benzamide;

(iii) N-[(1-cyclopropylmethyl 2-pyrrolidinyl)methyl]2-methoxy 4-[(1-H 4,5-dihydro 2-imidazolyl-)amino]5-chloro benzamide;

(iv) N(1-allyl 2-pyrrolidinyl methyl)2-methoxy 4-[(1-H 4,5-dihydro 2-imidazolyl)amino]5-chloro benzamide;

(v) N-(1-ethyl 2-pyrrolidinyl methyl) 2-methoxy 4-[4,5-dihydro 1,3-thiazol 2-yl)amino]5-chloro benzamide;

(vi) N-(1-cyclopropylmethyl 2-pyrrolidinylmethyl)2-methoxy 4-[(4,5-dihydro 2-oxazolyl)amino]5-chloro benzamide; and (vii) N-allyl 2-methoxy 4-[(1-H 4,5-dihydro 2-imidazolyl)amino]5-chloro benzamide.

The benzamide compounds of this invention may be prepared by reacting:

(1) an acid or a reactive derivative of an acid of general formula (II):

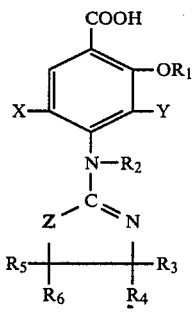

wherein $R_1$, $R_2$, $R_3$, $R_4$, $R_5$, $R_6$, X, Y and Z each have the same meaning as set forth in formula (I), with (2) an amine or a reactive derivative of an amine of general formula (III):

A—NH$_2$      (III)

wherein A has the same meaning as in formula (I) above. The acid function group may also be amidified before substituents X, Y or $R_2$ are fixed on the molecule.

The method of preparing the benzamides of this invention more specifically comprises:

(a) reacting a compound of the formula (IC):

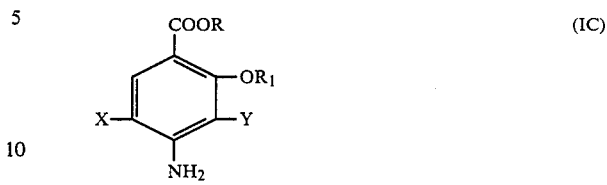

with thiophosgene to produce a 4-isothiocyanato benzoate of formula (IV):

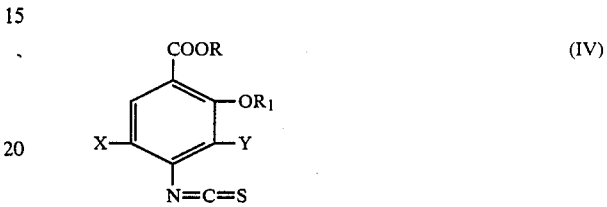

(b) reacting the formula (IV) compound with a compound of formula (ID):

wherein B is an amino or hydroxy group, to produce a compound of formula (V):

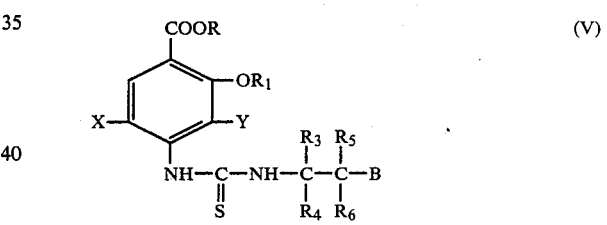

(c) ring-closing the formula (V) compound to form a compound of formula (VI):

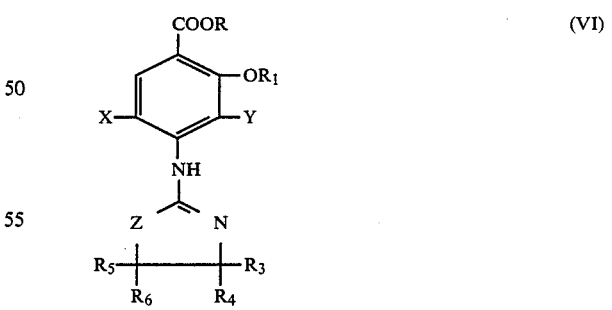

wherein R is alkyl, and $R_1$, X, Y, Z and $R_3$-$R_6$ are the same as set forth above for formula I and;

(d) amidifying the formulaa (VI) compound to obtain the corresponding formula (I) compound, werein $R_2$ is a hydrogen atom or optionally, wherein the $R_2$ hydrogen atom is converted to an $C_1$-$C_6$ alkyl or $C_2$-$C_6$ alkenyl group.

A preferred method of making the benzamides of this invention includes converting a formula (VI) compound to a compound of formula (VI)A as shown below:

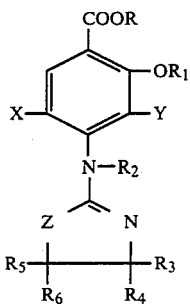
(VI)A wherein $R_2$ is $C_1-C_6$ alkyl or $C_2-C_6$ alkenyl. This conversion takes place after step (c) and prior to step (d), as described above.

Novel intermediate products are produced during the preparation of the benzamides of this invention. These include:

(i) a 4-isothiocyanato benzoate intermediate product having the general formula (IV):

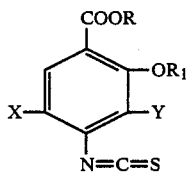
(IV)

wherein R is an alkyl; $R_1$ a hydrogen atom, $C_2-C_6$ alkenyl or $C_1-C_6$ alkyl; X is a haogen atom; and Y is a hydrogen or halogen atom.

(ii) an intermediate product having the general formula (V):

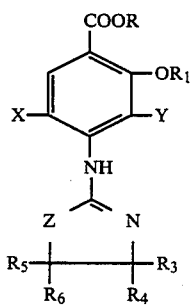
(V)

wherein B is an amino or hydroxy; R is alkyl; $R_1$ is a hydrogen atom, $C_1-C_6$ alkyl or $C_2-C_6$ alkenyl; X is a halogen atom; Y is a hydrogen atom or haogen atom and $R_3-R_6$ are each a hydrogen atom or $C_1-C_6$ alkyl.

(iii) an intermediate product having the general formula (VI):

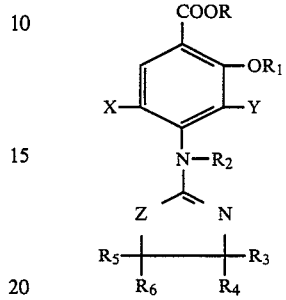
(VI)

wherein R is an alkyl; $R_1$ is a hydrogen atom, $C_1-C_6$ alkyl, or $C_2-C_6$ alkenyl; X is a halogen atom; Y is a hydrogen or halogen atom; $R_3-R_6$ are each a hydrogen atom or $C_1-C_6$ alkyl; and Z is a NH group or an oxygen or sulfur atom.

(iv) an intermediate product having a general formula (VI)A:

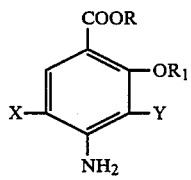
(VI)A wherein R is an alkyl; $R_1$ is a hydrogen atom, $C_1-C_6$ alkyl, $C_2-C_6$ alkenyl, X is a halogen atom; Y is a hydrogen or halogen atom; $R_2$ is $C_1-C_6$ alkyl or $C_2-C_6$ alkenyl; $R_3-R_6$ are each hydrogen atom or $C_1-C_6$ alkyl; and Z is a NH group or an oxygen or sulfur atom.

A more preferred method of preparing the benzamide compounds of this invention and formula 1 is where Z represents a NH group, anc comprises the steps of:

(a) formylating a compound of formula (IC)

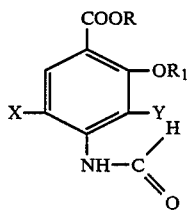
(IC)

to produce an alkyl 4-formylamino benzoate of formula (VII):

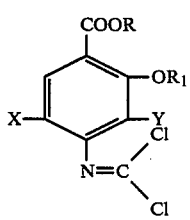
(VII)

(b) converting the alkyl 4-formylamino benzoate to an alkyl 4-dichloroformylimino benzoate of formula (VIII):

COOR (VIII)
OR₁
X—⟨ring⟩—Y
        Cl
        /
   N=C
        \
        Cl (c) converting the alkyl 4-dichloroformylimino benzoate of formula VIII to an alkyl 4-[(1-H 4,5-dihydro 2-imidazolyl)amino]benzoate of formula (VI):

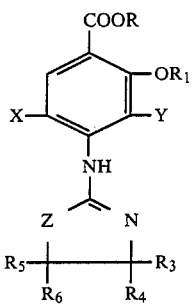

(VI)

(d) amidifying the formula (VI) compound to obtain a corresponding benzamide of formula I, wherein $R_2$ is a hydrogen atom, or optionally, the $R_2$ group is converted from hydrogen to an alkyl or alkenyl group and wherein R is alkyl, $R_1$, X, Y are the same as set forth in Formula I above; and Z is a NH group.

This method also includes the steps of (i) converting the formula (VI) compound formed in step (c) above to its formula (VI)A derivative having the formula:

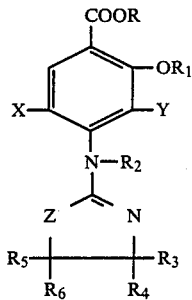

(VI)A wherein R is an alkyl; $R_1$ is a hydrogen atom, $C_1$–$C_6$ alkyl, $C_2$–$C_6$ alkenyl; X is a halogen atom; Y is a hydrogen or halogen atom; $R_2$ is $C_1$–$C_6$ alkyl or $C_2$–$C_6$ alkenyl; $R_3$–$R_6$ are each a hydrogen atom or $C_1$–$C_6$ alkyl; and Z is a NH group, and (ii) amidifying the formula (VI)A compound to obtain the corresponding formula (I) compound.

Additional novel intermediate products produced during preparation of the benzamides of this invention include:

(i) an intermediate product having a general formula (VII) as follows:

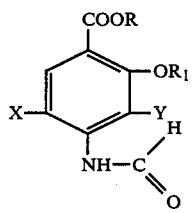

(VII)

wherein R is alkyl, $R_1$ is a hydrogen atom, $C_1$–$C_6$ alkyl or $C_2$–$C_6$ alkenyl; X is a haogen atom; and Y is a halogen or hydrogen atom; and (ii) an intermediate product of formula (VIII) as follows:

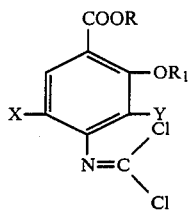

(VIII)

wherein R is alkyl, $R_1$ is a hydrogen atom, $C_1$–$C_6$ alkyl or $C_2$–$C_6$ alkenyl; X is a halogen atom; and Y is a hydrogen or halogen atom.

The reactive derivatives of formula (II) acids which can be used in synthesizing the compounds of the invention include derivatives such as the acid halide, alkyl ester, reactive ester such as methoxymethyl or cyanomethyl ester, aromatic ester, N-hydroxy imide ester, symmetric anhydride or mixed anhydride formed e.g. from a carboxylic acid ester or a haloformic ester, azide, hyrazide or azolide.

The reactive derivatives of formula (III) amines which can be used for synthesizing the benzamides include derivatives such as those obtained by previously reacting the amine with a phosphorus chloride, phosphorus oxychloride, a dialkyl-, diaryl- or orthophenylene-chlorophosphite, an alkyl- or aryl-dichlorophosphite, or the isothiocyanate of the amine.

The invention is not restricted to the acid and amine derivatives mentioned above.

The amidifying reaction may be carried out in situ or when the intermediate reactive derivatives have been isolated. The amidifying reaction may be carried out with or without any solvent.

It is also possible for the free acid and the free amine to be reacted in the presence of a conventional condensing agent such as silicon tetrachloride, phosphoric anhydride, a carbodiimide or an alkoxy acetylene.

The systems used as solvents, which are inert relative to the amidifying reaction, may, for example, be alcohols polyols, ketones, benzene, toluene, dioxane, chloroform, or diethylene glycol dimethyl ether. An excess of the amine used as starting material may equally be used as the solvent. It may be preferable to heat the reaction mixture during amidification, e.g. to the boiling point of the above mentioned solvents.

In one of the preferred embodiments of the invention the formula (I) compounds are prepared by different methods from the same starting materials:

In the first embodiment, alkyl 4-amino 5-halo benzoate is treated with thiophosgene to give alkyl 4-isothiocyanato 5-halo benzoate (IV), which is converted to alkyl [4-N-amino (or hydroxy) alkyl]thioureido 5-halo benzoate (V), and then converted to alkyl 4-[4,5-dihydro 2-imidazolyl (or 2-thiazolyl or 2-oxazolyl) amino] 5-halo benzoate (VI) and finally converted to 4-[4,5-dihydro 2-imidazolyl (or 2-thiazolyl or 2-oxazolyl) amino] 5-halo benzamide (I).

In the second embodiment, alkyl 4-amino 5-halo benzoate is treated with formic acid to give alkyl 4-formylamino 5-halo benzoate (VII), which is converted to alkyl 4-dichloroformylimino 5-halo benzoate (VIII), and then converted to alkyl 4-(1-H 4,5-dihydro 2-imidazolyl) amino benzoate (VI), and finally converted to a formula (I) benzamide where Z represents an NH group.

In these syntheses the formula (IV), (V), (VI), (VII), (VIII) intermediate compounds are novel, and include those that are 3,5-dihalogenated.

The technical characteristics of the invention are illustrated in the following examples. These are shown to illustrate the invention but are not meant to restrict the invention to these particular examples.

EXAMPLE I

N-[(DIETHYL AMINO) ETHYL] 2-METHOXY 4-[(1-H 4,5-DIHYDRO 2-IMIDAZOLYL) AMINO] 5-CHLORO BENZAMIDE

Stage I: METHYL 2-METHOXY 4-ISOTHIOCYANATO 5-CHLORO BENZOATE 450 cc of water, 318 g of methyl 2-methoxy 4-amino 5-chloro benzoate, 155 g of calcium carbonate, 900 cc of dichloroethane and 195.5 g of thiophosgene are placed in a four liter three-necked flask fitted with an agitator, a thermometer and a reflux condenser.

The mixture is agitated and heated gently. The reaction starts at about 30°–35° C. Heating is stopped at 40° C. but the temperature rises to 48°–50° C. The material is cooled to 40° C. with a bath of water and ice and a temperature of 40° C. is maintained for about 15 minutes. The amount of gas given off decreases. The material is heated slowly to reflux at 75° C. and left for two hours. The liberation of $CO_2$ stops after about 1 hour reflux.

The reaction medium is cooled to about 30° C. and decanted, and the aqueous phase is washed with 100 cc of dichloroethane.

The organic phases are combined, one liter of water is added and the azeotrope is distilled under vacuum until all the dichloroethane has come off. The aqueous suspension is drained, washed with water then resuspended in one liter of petroleum ether. It is then agitated for 15 minutes, drained, washed with petroleum ether and dried at 50° C.

364 g of product is obtained (yield=95.8%).
Melting point=90° C.
NMR=Compatible, no impurity found.

Stage II: METHYL 2-METHOXY 4-(N'2-AMINO ETHYL)-THIOUREIDO 5-CHLORO BENZOATE 13.4 ml (0.2 mole) of ethylene diamine and 300 ml of isopropyl ether are placed in a one liter three-necked flask fitted with an agitator, a thermometer and a filling funnel and cooled to 0° C., −5° C. A solution of 25.75 g (0.1 mole) of methyl 2-methoxy 4-isothiocyanato 5-chloro benzoate in 150 ml of toluene is dripped in at that temperature for 30 minutes.

The mixture is agitated for a further 2 hours at 5° C. The precipitate is drained and returned to the flask in a moist state with 250 cc of water. It is agitated for 14 minutes at 5° C., drained, washed with water and dried at 50° C.

29.7 g of product is obtained (93.5%).
Melting point=80°–90° C.
Titer=91.1%.
S=9.35% (calculated 10.08%).
Yield of pure product=85.2%.

Stage III: METHYL 2-METHOXY 4-[(1-H 4,5-DIHYDRO 2-IMIDAZOLYL) AMINO] 5-CHLORO BENZOATE 322.2 g (approximately 0.92 mole) of methyl 2-methoxy 4-(N'2-aminoethyl)-thioureido 5-chloro benzoate and 645 ml of water are placed in a 4 liter, three-necked flask fitted with an agitator, a thermometer, a reflux condenser and a filling funnel. The suspension is heated to 70°–75° C. and 461.6 g (1.218 mole) of lead acetate solution in 1.8 liter of distilled water is poured in over the course of one hour. The mixture is kept at 70°–75° C. for 2 hours then cooled to 20° C. The lead sulphide is drained, washed with water and dried (258.1 g).

The filtrate is transferred to a six liter, three-necked flask and a solution of 132.5 g of sodium carbonate (1.25 mole) in one liter of water, previously treated with carbon black and filtered, is stirred in. Agitation is continued for one hour (pH 7–8), then the precipitate is filtered, washed and dried, yielding 79.5 g.

The mother liquor is reacted with a further 132.5 g of sodium carbonate and the precipitate obtained is drained, washed and dried, yielding 210.4 g of crystals which melt at 216°–217° C.

Total yield: 80.4%.

Stage IV: N-[2-(DIETHYL AMINO) ETHYL] 2-METHOXY 4-[1-H 4,5-DIHYDRO 2-IMIDAZOLYL) AMINO] 5-CHLORO BENZAMIDE 28.35 g (0.1 mole) of methyl 2-methoxy 4-[(1-H 4,5-dihydro 2-imidazolyl) amino] 5-chloro benzoate, 28 ml of ethylene glycol and 12.76 g (0.11 mole) of diethyl amino ethylamine are placed in a 250 ml three-necked flask and agitated for 48 hours at 70°–75° C. 50 cc of water is added and the mixture is cooled to 10° C., drained, washed with water and dried.

This yields 30.7 g of a material which melts at 185°–190° C. (83.5%)

22.3 g of the material is heated to boiling point with 100 cc of water and 3 cc of sodium hydroxide for 15 minutes, then filtered at 60° C. The precipitate is washed with water and dried.

19.8 g of obtained (88.8%).
(Melting point=198° C.).
NMR is compatible, no ester found.

17.8 g of the material is dissolved hot in 240 cc of dichloroethane, treated with 3 S ACTI CARBONE black, crystallized cold (−10° C.), drained, washed with dichloroethane and dried at 50° C.

The material still containing dichloroethane is re-dried twice for 48 hours at 70° C., after which there is still some dichloroethane.

Weight obtained: 12.2 (yield 64.2%).

The material is made into a paste with acetone at 60° C., cooled, filtered and washed with acetone and dried for 48 hours at 70° C., giving 9.7 g.

Büchi melting point: 190.5–191.5.
Kofler melting point: 194°–195° C.
NMR: compatible; still contains a small amount of dichloroethane.
Titer: 98.4%.
CCM: 3 secondary marks—

| Rf. | 0.22 | < | 0.1% |
|---|---|---|---|
| | 0.37 | | 0.1% |
| | 0.75 | < | 0.1% |

EXAMPLE II

N-[2-(DIETHYL AMINO) ETHYL] 2-METHOXY 4-[N-ETHYL, N-(1-H 4,5-DIHYDRO 2-IMIDAZOLYL) AMINO] 5-CHLORO BENZAMIDE 42 g (0.114 mole) of N-(diethyl amino ethyl) 2-methoxy 4-[(1-H, 4,5-dihydro 2-imidazolyl) amino] 5-chloro benzamide, 100 ml of methanol, and 24.8 g (0.228 mole) of ethyl bromide are placed in a 250 ml autoclave and heated to 100° C. with agitation. The pressure rises to 10 kg, then drops back to 6 kg. The temperature stabilizing at 90° C. Agitation is continued for 6 hours; the mixture is cooled and the methanol removed under vacuum. The residue is dissolved in 100 ml of water and made alkaline while cooling, with 25 g of potassium hydroxide pellets.

150 ml of methylene chloride is stirred in. A precipitate forms and is drained and washed with 50 ml of methylene chloride. The filtrate is decanted and the aqueous phase is washed with 50 ml of methylene chloride. The solvent is removed dry under vacuum and the oily residue agitated with 100 ml of isopropyl ether, crystallizes. The precipitate is drained, washed with 50 ml of isopropyl ether and dried, giving 22 g of product (yield=48.8%).

Melting point=135° C.

NMR: Compatible; contains 2 to 3% of starting material.

The material is dissolved hot in 90 cc of ethyl acetate, treated with 3 S ACTI CARBONE black, crystallized cold (−10° C.), drained, washed with isopropyl ether and dried.

This yields:

16.2 g of product (yield=73.6%).
Melting point (Kofler)=136° C.
Weight loss (100° C.)=0.12%.
Titer=99.1%.
Cl=8.93%—Calculated 8.95%.
N=17.76%—Calculated 17.69%.
The NMR and IR spectra are compatible.

EXAMPLE III

N-[2-(DIETHYLAMINO) ETHYL] 2-METHOXY 3,5-DIBROMO 4-[(1-H 4,5-DIHYDRO 2-IMIDAZOLYL) AMINO] BENZAMIDE

Stage I: METHYL 2-METHOXY 4-ISOTHIOCYANATO 5-BROMO BENZOATE 260 g (1 mole) of methyl 2-methoxy 4-amino 5-bromo benzoate, 110 g (1,1 mole) of calcium carbonate, 300 cc of water, 600 cc of 1-2 dichloro ethane and 88 cc (132 g, i.e. 1.15 mole) of thiophosgene are placed in a 2 liter three-necked flask fitted with an agitator, a thermometer, a reflux condenser and a trap.

The mixture is heated gently. The liberation of carbon dioxide starts at about 30°–35° C. Heating is stopped at 40°˚C. and a temperature of 40° C. is maintained for about one hour with a water bath. The amount of gas given off decreases. The material is heated to reflux (70°–75° C.) slowly, in one hour, and left at that temperature for 3 hours. It is cooled to 45°–50° C., filtered if slightly insoluble and decanted. The aqueous phase is washed with 100 ml of dichloroethane.

300 cc of water is added to the organic phase and the solvent is removed under vacuum. The aqueous suspension is drained, washed and stirred into suspension in 600 cc of petroleum ether. It is then redrained, washed with petroleum ether and dried at 50° C.

290.09 g of product is obtained (Yield=96%).
Melting point=99.
NMR compatible, No impurity found.
S %=10.16 (calculated 10.59).

Stage II: METHYL 2-METHOXY 4-(N' 2-AMINO ETHYL) THIOUREIDO 5-BROMO BENZOATE 1.1 liters of isopropyl ether and 63.5 g (1.06 mole) of ethylene diamine are placed in a 2 liter three-necked flask fitted with an agitator, a thermometer and a filling funnel, and cooled to 0° C. A filtered solution of 106.6 g (0.351 mole) of methyl 2-methoxy 4-isothiocyanato 5-bromo benzoate in 350 ml of toluene is stirred in drop by drop in the course of 30 minutes while the temperature is kept at 0° C. The mixture is agitated at that temperature for 1 hour, then the solvents are separated. Rubbery material is left on the walls, 1 liter of water is poured into the flask and is agitated for half an hour. The product crystallizes; it is drained, washed with water then dried at 50° C.

85.7 g of product is obtained (Yield=67.4%).
Melting point=80°–90° C. (pasty).
Titer=90.4%.
S%=8.10 (calculated 8.84).

Stage III: METHYL 2-METHOXY 4-[(1-H 4,5-DIHYDRO 2-IMIDAZOLYL) AMINO] 5-BROMO BENZOATE 65 g (0.167 mole) of methyl 2-methoxy 4-(N'2-amino ethyl) thioureido 5-bromo benzoate (titer 98.8%) and 60 ml of water are placed in a 1 liter three-necked flask fitted with an agitator, a thermometer and a filling funnel, and heated to 70° C. with agitation. 75 g (0.198 mole) of lead acetate dissolved in 30 cc of distilled water is poured in at that temperature in the course of 30 minutes.

The material is agitated for 2 hours at 70°–80° C. then cooled to 20° C. The lead sulphide is filtered and washed with water (46.74 g of dried sulphide). The filtrate is treated with 15 g of sodium carbonate in 150 cc of water (pH 6–7). The precipitate is drained, washed and dried (11.16 g of salts). The filtrate is made alkaline with 27.4 g of sodium carbonate and agitated for 10 minutes. The precipitate is drained, washed and dried.

47.92 g of product is obtained. (Yield: 87.7%).
Melting point=214° C.
Titer=98%.
NMR compatible.

Stage IV: METHYL 2-METHOXY 3,5-DIBROMO 4-[(1-H 4,5-DIHYDRO 2-IMIDAZOLYL)-AMINO] BENZOATE 362 g (1.1 mole) of methyl 2-methoxy 4-[(1-H 4,5-dihydro 2-imidazolyl) amino] 5-bromo benzoate, 550 ml of acetic acid and 256 g (1.43 mole) of N-bromo succinimide are stirred into a three-necked flask. The mixture is heated to 55° C., agitated at that temperature for 5 hours then left to stand at 55° C. for 70 hours.

The reaction material is cooled and stirred into 5 liters of water. The insoluble material is drained off and washed. The filtrate is made alkaline with 750 ml of soda lye (pH 6) while it is cooled with ice, then with 230 g of sodium carbonate, to pH 9–10. The precipitate formed is drained, washed with water and dried.

416 g is obtained (yield=92.44%).

Br=39.63% (calculated 39.31%).
Kofler melting point=193° C. (slight partial melting at 170° C.).
NMR=Compatible.

Stage V: N-[2-(DIETHYL AMINO) ETHYL] 2-METHOXY 3,5-DIBROMO 4-[(1-H 4,5-DIHYDRO 2-IMIDAZOLYL) AMINO] BENZAMIDE 30.5 g (0.075 mole) of methyl 2-methoxy 3,5-dibromo 4-](1-H 4,5-dihydro 2-imidazolyl) amino] benzoate, 50 cc of ethylene glycol and 17.4 g (0.15 mole) of diethyl amino ethyl amine are placed in a 250 cc three-necked flask and agitated for 72 hours at 70°-75° C. 150 cc of water is added, then the mixture is cooled to 10° C., drained, washed with water then acetone and dried.

18.7 g is obtained (yield=50.8%).
NMR: compatible.
Titer=99.7%.

18 g is dissolved hot in 15 volumes (270 cc) of methyl ethyl ketone, treated with black, filtered, crystallized cold, drained, washed with acetone and dried.

14.5 g is obtained (purification yield=80.7%).
Melting point (Kofler)=192° C.
Weight loss at 100° C.=0.07%
Titer=99.7%.
Br=32.49% (calculated 32.49%).
N=14.17% (calculated 14.26%).
The NMR and IR spectra are compatible.

EXAMPLE IV

N-[2-(DIETHYL AMINO) ETHYL] 2-METHOXY 3,5-DICHLORO 4-[(1-H, 4,5-DIHYDRO 2-IMIDAZOLYL) AMINO] BENZAMIDE

Stage I: METHYL 2-METHOXY 4-FORMYLAMINO 5-CHLORO BENZOATE 829 g (768 ml or 8.13 moles) of acetic anhydride (d=1.08) is placed in a three liter flask fitted with an agitator, a thermometer, a condenser and a bromine funnel, and 1,444 g (1184 ml or 31.4 moles) of formic acid (d=1.22) is poured in in a fine stream.

The reaction is exothermic (40° C.). The reaction medium is then heated for 1 hour at 50° C. and cooled to between 5° and 10° C. 345 g (1.6 mole) of methyl 2-methoxy-4-amino 5-chloro benzoate is added in stages. It is then heated for 2.5 hours at 50° C. and cooled to 20° C. and the solution is poured into 10 liters of water. The precipitate is drained, washed with water and dried in an oven at 50° C.

Yield=366 g (94%).
Melting point=150° C. (Kofler).

Stage II: METHYL 2-METHOXY 3,5-DICHLORO 4-DICHLORO FORMYLIMINO BENZOATE 443 g (270 ml or 3.72 moles) of thionyl chloride and 161.3 g (96 ml or 1.68 mole) of sulfuryl chloride are placed in a one liter flask fitted with an agitator, a thermometer and a condenser connected to a soda bubbler. They are cooled to 0° C. and 121.7 g (0.50 mole) of methyl 2-methoxy 4-formylamino 5-chloro benzoate is added in stages over about 10 minutes until the benzoate dissolves. The solution is agitated for 90 minutes, with the cold bath removed, and is left to stand overnight at 15° C. The solvents are evaporated under vacuum with the mass not exceeding 30° C. A powdery residue is obtained and is used without purification (weight=163 g).

Stage III: METHYL 2-METHOXY 3,5-DICHLORO 4-[(1-H 4,5-DIHYDRO 2-IMIDAZOLYL) AMINO] BENZOATE 89.9 g (1.50 moles) of ethylene diamine, and 1000 ml of ethyl acetate are placed in a two liter flask fitted with an agitator, a thermometer, a condenser and a bromine funnel. The mixture is cooled to −20° C. and the product obtained in Stage II is added in a fine stream in 500 ml of ethyl acetate, taking about 15 minutes.

An orange precipitate forms when the adding process starts. When it is over the precipitate sets around the agitator and blocks it. It is left in contact for 15 minutes at −20° C., then the temperature is raised to 0° C. and a solution of 300 ml of hydrochloric acid (d=1.18) in 500 ml of water is added.

The aqueous phase is decanted, extracted twice with 250 ml of methylene chloride, then 200 g of ice and 50 ml of methylene chloride are added to it. It is made alkaline with 300 ml of ammonia (d=0.90), without exceeding 10° C.

The reaction medium is agitated for 45 minutes between 5° and 10° C. and the precipitate is drained, washed five times with 40 ml of water and oven-dried at 50° C.

Yield=21 g (13%).
Melting point=207° C.
Cl % found=22.90, Calculated 22.23.
Titer % found=93.4, Calculated 100.

Stage IV: N-[2-(DIETHYLAMINO) ETHYL] 2-METHOXY 3,5-DICHLORO 4-[(1-H 4,5-DIHYDRO 2-IMIDAZOLYL) AMINO] BENZAMIDE 23 g (0.072 mole) of methyl 2-methoxy 3,5-dichloro 4-[(1-H 4,5-dihydro 2-imidazolyl) amino] benzoate, 40 ml of glycol, 16.7 g (0.144 mole) of NN-diethyl amino ethylamine and 3 drops of hydrochloric acid (d=1.18) are placed in a 250 ml flask fitted with an agitator, a thermometer and a condenser. The mixture is heated for 67 hours at 75° C. and cooled, and the suspension is poured into 300 ml of water. The crystals are drained, washed with water (4 times with 30 ml) and oven-dried overnight at 50° C.

Yield=10.6 g. (36.5%).
Melting point=187° C. (Kofler).

22.6 g of the product is dissolved in 66 ml of 80% ethanol at boiling temperature. It is filtered through vegetable charcoal and the filtrate is left to crystallize overnight in a refrigerator. The solid is drained, washed twice with 5 ml of the recrystallizing solvent and oven-dried at 50° C.

Yield=18.8 g (83%).
Melting point=187° C. (Kofler).

|  | Calculated | Found |
| --- | --- | --- |
| H₂O % |  | 0.1 |
| Titer % | 100 | 199.2 |
|  |  | 2 |
| Cl % | 17.62 | 17.62 |

EXAMPLE V

N-[(1-ETHYL 2-PYRROLIDINYL) METHYL] 2-METHYOXY 3,5-DIBROMO 4-[(1-H 4,5-DIHYDRO 2-IMIDAZOLYL) AMINO] BENZAMIDE 81.4 g (0.2 mole) of methyl 2-methoxy 3,5-dibromo 4-[(1-H 4,5-dihydro 2-imidazolyl) amino]benzoate, 80 ml ethylene glycol, and 51.2 g (0.4 mole) of 1-ethyl 2-amino methyl pyrrolidine are placed in a 500 ml, three-necked flask and agitated for 72 hours at 70°–75° C.

The reaction medium is cooled and the back paste is extracted with 3×150 ml of ethyl ether. The solvent is evaporated from the extract under vacuum to give 20 g of a paste which crystallizes in 100 ml of isopropyl ether. It is drained, washed with isopropyl ether and cried, to give 6.8 g of crystals with melt at 115° C. The black paste left in the ethylene glycol is recovered with 150 ml of water and extracted with 5 times 200 ml of methylene chloride. The solvent is dried over magnesium sulphate and evaporated under vacuum. The residue (78.7) is dissolved hot in 150 ml of ethyl acetate crystallized cold. It is filtered, washed with isopropyl ether and dried. 29.65 g of the product to be purified is obtained. The aqueous mother liquors crystallize. They are drained, washed and dried and 8 g of crystal is obtained.

The three streams (43 g) are dissolved hot in 130 ml of isopropanol, treated with carbon black, crystallized overnight in a refrigerator, washed and dried. 22.1 g of product (yield=22%), melting 180° C. is obtained and purified. For this purpose 26.6 g of product is dissolved hot in 185 ml of methyl ethyl ketone, treated with black, crystallized cold, drained, washed with methyl ethyl ketone and dried, 18.6 g of beige crystals is recovered. They are crystallized again in methyl ethyl ketone with carbon black treatment, 13.1 g of crystals is obtained (purification yield=49.3%).

Melting point=180° C. (Kofler).
Corrected titer=98.5%.

| Br = 32.47 | corrected = | 32.50% |
| | calculated = | 31.75% |
| N = 13.68% | corrected = | 13.69% |
| | calculated = | 13.92% |

The NMR and IR spectra are compatible.

EXAMPLE VI

N-[2 (DIETHYL AMINO) ETHYL] 2-METHOXY 4-[N-ALLYL, N-(1-H 4,5-DIHYDRO 2-IMIDAZOLYL) AMINO] 5-CHLORO BENZAMIDE

Stage I: METHYL 2-METHOXY 4-[N-ALLYL, N-1-H 4,5-DIHYDRO 2-IMIDAZOLYL) AMINO] 5-CHLORO BENZOATE (HYDRO BROMIDE)

113.4 g (0.4 mole) of methyl 2-methoxy 4-[(1-H, 4,5-dihydro 2-imidazolyl)amino] 5-chloro benzoate, 400 ml of methanol and 96.8 g (0.8 mole) of allyl bromide are placed in a one liter autoclave and heated to 100° C. with agitation for 18 hours. The reaction medium is cooled and the solvent is evaporated under vacuum. The pasty residue is recovered with 200 ml of acetone, agitated, drained, washed with 200 ml of acetone and dried.

103.2 g of product are obtained (yield=63.8%) with the following properties:
Melting point=226° C. instantly then 220.
Titer=99%.
H Br=19.53% (calculated 20.02%).
NMR=compatible.

Stage II: N-[2-(DIETHYL AMINO) ETHYL] 2-METHOXY 4-[N-ALLYL, N-(1-H 4,5-DIHYDRO 2-IMIDAZOLYL) AMINO] 5-CHLORO BENZAMIDE 40.45 g (0.1 mole) of methyl 2-methyoxy 4-[N-allyl, N-(1-H 4,5-dihydro 2-imidazolyl) amino] 5-chloro benzoate hydrobromide, 40 ml of ethylene glycol and 34.8 g (0.3 mole) of diethyl amino ethyl amine are placed in a 500 ml three-necked flask and agitated for 72 hours at 70°–75° C. The reaction medium is cooled and 110 ml of soda lye is added. The medium is then recooled to 5° C. and 150 ml of ethyl ether is added and the emulsion formed is filtered. The cake is washed with 300 ml of water and dried.

12.6 g is obtained (yield=30.9%).
Melting point=142° C.
NMR=compatible (small amount of aromatic impurity).

The ethyl ether is evaporated from the filtrate and the filtrate is extracted with 200 ml, then 2 times 100 ml of methylene chloride.

The organic phase is dried over magnesium sulphate and evaporated under vacuum. The residue is recovered in 100 ml of isopropyl ether, filtered, washed two times with 50 ml of isopropyl ether and dried at 50° C. 12.6 g of the product is obtained (yield 30.9%).

Melting point=140° C.
NMR=compatible (no impurity found).

34.4 g of the product is dissolved hot in 200 ml of isopropyl acetate, treated with black, crystallized overnight in a refrigerator, drained, washed with isopropyl acetate and dried.

27.6 g of purified product is obtained. It is crystallized again, treated with carbon black twice and dried at 60° C.

16.5 g of product is obtained (purificaion yield=48%).
Melting point=141° C.
Titer=98.9%.
NMR=Compatible.

EXAMPLE VII

N-[(1-ETHYL 2-PYRROLIDINYL) METHYL)] 2-METHOXY 4-[N-ALLYL, N-(1-H, 4,5-DIHYDRO 2-IMIDAZOLYL) AMINO] 5-CHLORO BENZAMIDE 60.68 g (0.15 mole) of methyl 2-methoxy 4-[(N-allyl, N-(1-H 4,5-dihydro 2-imidazolyl) amino] 5-chloro benzoate, 60 ml of ethylene glycol and 38.4 g (0.3 mole) of 1-ethyl 2-aminomethyl pyrrolidine are placed in a 500 ml three-necked flask and agitated for 72 hours at a temperature of 70°–75° C. The reaction medium is cooled and 15 ml of soda lye is added. The blackish mass is extracted first with 200 ml, and then two times with 100 ml of ethyl ether. The solvent is concentrated dry under vacuum to give 19.6 g of oil (excess of initial amine). The aqueous phase is diluted with 150 ml of water and extracted first with 200 ml, then two times with 100 ml of methylene chloride. The solvent is dried over magnesium sulphate and removed under vacuum.

The pasty residue is crystallized in 300 ml of isopropyl ether, drained (rubbery substance), formed into a paste in 50 ml of isopropyl acetate, drained, washed with 50 ml of isopropyl acetate and dried at 50° C.

21.6 g of product melting at 123° C. is obtained (yield=34.3%).

NMR=compatible (impurity at the limit of detection).

27.3 g of product is then dissolved hot in 60 ml of isopropyl acetate, treated with black, crystallized overnight in a refrigerator, drained, washed with isopropyl ether and dried. After a second crystallization in 36 ml of isopropyl acetate, 7.9 g of beige material is obtained (purification yield=29%).

Melting point=120–122% (not clearly defined).
Titer=98.2%.
NMR=Compatible (uncompleted resolution).

EXAMPLE VIII

N-[(1-CYCLOPROPYLMETHYL 2-PYRROLIDINYL) METHYL] 2-METHOXY 3,5-DICHLORO 4-[(1-H 4,5-DIHYDRO 2-IMIDAZOLYL) AMINO] BENZAMIDE

Stage I: METHYL 2-METHOXY 4-ACETAMINO 3,5-DICHLORO BENZOATE 256 g (1 mole) of methyl 2-methoxy 4-acetamido 5-chloro benzoate and 1000 cc of acetic acid are placed in a one liter flask fitted with an agitator and a thermometer. A suspension is obtained and 177 g (1 mole+30% excess) of chlorosuccinimide is added in one operation. It is treated in a water bath at 50° C.–55° C. for two hours until everything dissolves. Agitation is then stopped and the reaction is allowed to continue in an even at 50° C.–55° C. for about 40 hours. Only traces of chlorosuccinimide are then left in solution (this is checked by quantitative analysis).

The reaction medium is cooled and diluted with about 10 liters of water: the ester is precipitated first as a liquid then as a solid. It is drained, washed with water and dried; weight obtained=237 g (yield=81%), melting point=132°–133° C.

After recrystallization in absolute alcohol 185 g of crystals is obtained, having a melting point of 141°–142° C. (yield 78%) Total yield 63%.

Stage II: METHYL 2-METHOXY 3,5-DICHLORO 4-AMINO BENZOATE 407 g (1.39 mole) of methyl 2-methoxy 3,5-dichloro 4-acetamido benzoate and 2215 ml of methanol are placed in a 6 liter flask fitted with an agitator, a thermometer, a condenser and a bromine funnel. 161 g (88 ml) of sulphuric acid (d=1.83) is poured in in a fine stream. The temperature rises to about 40° C. The reaction mixture is heated under reflux (65° C.) for 21 hours, cooled to 20° C. and poured into a reactor containing 3500 g of water and 1500 g of ice. The product crystallizes. It is drained, washed with water and oven-dried at 50° C. Yield=88% (i.e. 305 g).

Melting point=69° C.

The NMR spectrum is compatible with the expected structure.

Cl %: found 28.09, calculated 28.40.

Stage III: METHYL 2-METHOXY 3,5-DICHLORO 4-FORMYLAMINO BENZOATE 630 g (6.2 moles) of acetic acid anhydride is placed in a 4 liter flask fitted with an agitator, a thermometer, a condenser and a bromine funnel, and 1083 g (23.5 moles) of formic acid is poured in a fine stream. The reaction is exothermic and the temperature goes from 23° to 47° C. when all the material has been added. The reaction mixture is heated for one hour at 50°–55° C. then cooled to 5° C., 305 g (1.22 mole) of methyl 2-methoxy 3,5-dichloro 4-amino benzoate is added in stages.

The temperature is brought back to ambient by removing the cold bath, and the reaction mixture heated for two and a half hours at 50°–55° C. It is then cooled to 20° C. and poured into a reactor containing 4400 ml of water and 1700 g of ice. The product crystallizes. It is drained, washed with water and oven-dried at 50° C.

Yield=312 g (92%).
Melting Point=136°–138° C.

Stage IV: METHYL 2-METHOXY 3,5-DICHLORO 4-[(1-H 4,5-DIHYDRO 2-IMIDAZOLYL) AMINO] BENZOATE 93 g (0.33 mole) of methyl 2-methoxy 3,5-dichloro 4-formyl amino benzoate, 386.5 g of thionyl chloride and 50.4 g of sulphuryl chloride are placed in a one liter flask fitted with an agitator, a thermometer and a condenser connected to a bubbling device containing potash pellets. The suspension is agitated for 22 hours at 20° to 25° C. (room temperature). It becomes totally soluble after a few hours reaction.

The excess reagents are evaporated under vacuum without being heated. 135 ml of ethyl acetate is added and again evaporated under vacuum without heating the solvent. 135 ml of ethyl acetate is added to the residual oil, and the solution obtained is poured into a reactor which is kept at about −15° C. and which contains 59.1 g of ethylene diamine and 390 ml of ethyl acetate. The cold bath is then removed and, when the temperature of the reaction mixture returns to 20° C., the suspension is poured slowly into a mixture of 196.5 ml of hydrochloric acid (d=1.18) and 132 ml of water. The temperature rises to 35° C. The mixture is cooled to no more than 30° C. then 475 ml of water is added and the organic phase is immediately decanted. The organic phase is washed with 120 ml of water, then the aqueous phases are combined and washed with 200 ml of methylene chloride.

The aqueous solution is cooled and neutralized to pH=9–10, without going above 30° C., with about 225 ml of ammonia (d=0.91).

The product is crystallized, drained then washed with water before being dried in an oven at 50° C.

Weight obtained=53 g.
Yield=50%.
Melting point=206° C.

Stage V: N-[(1-CYCLOPROPYLMETHYL 2-PYRROLIDINYL) METHYL] 2-METHOXY 3,5-DICHLORO 4-[(1-H 4,5-DIHYDRO 2-IMIDAZOLYL) AMINO] BENZAMIDE 23.3 g (0.073 mole) of methyl 2-methoxy 3,5-dichloro 4-[(1-H 4,5-dihydro 2-imidazolyl) amino] benzoate, 22.5 g of 1-cyclopropylmethyl 2-aminomethyl pyrrolidine and 200 ml of methanol are placed in a one liter flask fitted with an agitator, a thermometer and a condenser. The mixture is heated for 10 days under reflux and the methanol is evaporated under vacuum. The colored oil obtained is dissolved in 150 ml of butyl acetate at 60° C. The solution is then frozen and left to crystallize for 24 hours at 20° C. after being seeded.

The product is drained, washed with a small quantity of ethyl acetate and oven-dried at 50° C. 22 g of crystals is obtained (yield=69%), with a melting point at 158°–160° C. The product may be recrystallized in 220 ml of a mixture prepared from 200 ml of ethyl acetate and 20 ml of methanol.

10 g of crystals is obtained.
Melting point=162° C.

EXAMPLE IX

N- [1- (1-CYCLOHEXENYLMETHYL) 2-PYRROLIDINYL METHYL] 2-METHOXY 4-[(1-H 4,5-DIHYDRO 2-IMIDAZOLYL) AMINO] 5-CHLORO BENZAMIDE

Stage I: 2-METHOXY 4-[(1-H 4,5-DIHYDRO 2-IMIDAZOLYL) AMINO] 5 CHLOROBENZOIC ACID 11.8 g of methyl 2-methoxy 4-[(1-H 4,5-dihydro 2-imidazolyl) amino] 5-chloro benzoate is treated with 20 ml of water and 50 ml of (N) soda lye for 2 hours at 70° C. It is then cooled to 20° C. and neutralized with hydrochloric acid in normal solution. The precipitate obtained is washed and dried to give the acid in monohydrate form. The crystals melt at 190°–200° C. with decomposition (yield=99%).

Stage II: N [[1-(1-CYCLOHEXENYLMETHYL) 2-PYRROLIDINYL] METHYL] 2-METHOXY 4-[(1-H 4,5-DIHYDRO 2-IMIDAZOLYL) AMINO] 5-CHLOROBENZAMIDE 4.85 g (0.018 mole) of 2-methoxy 4-[(1-H 4,5-dihydro 2-imidazolyl) amino] 5-chloro benzoic acid, 50 ml of acetone and 5.45 g (0.054 mole) of triethyl amine are placed in a 250 ml flask fitted with an agitator, a thermometer, a condenser and a bromine funnel. A suspension is obtained and 5.8 g (0.054 mole) of ethyl chloroformate is dripped in with the temperature kept at 20° C. The mixture is then agitated for 45 minutes at 20° C. and 4.2 g (0.021 mole) of 1-(1-cyclohexenylmethyl) 2-aminomethyl pyrrolidine is dripped in at 20° C. (cooled).

The suspension obtained is agitated for one hour and left to stand overnight. 108 ml of (N)soda is added, the acetone is removed under vacuum and the pasty product is drained and recovered in a mixture of 2 ml of soda lye, 50 ml of ethanol and 20 ml of water. It is heated under reflux for 30 minutes, and 70 ml of water is added. The ethanol is evaporated under a vacuum and the crystals are drained, washed with water and oven-dried at 50° C.

Yield=4.9 g (61%).
Melting point=181° C.
The material is recrystallized in 60 ml of 95% ethanol.
Yield=3.1 g.
Melting point=190° C.
NMR spectrum compatible with expected structure.

EXAMPLE X

N-[[1-(1-CYCLOHEXENYL METHYL) 2-PYRROLIDINYL] METHYL] 2-METHOXY 3,5-DICHLORO 4-[(1-H 4,5-DIHYDRO 2-IMIDAZOLYL) AMINO] BENZAMIDE 4.5 g (0.015 mole) of 2-methoxy 3,5-dichloro 4-[(1-H 4,5-dihydro 2-imidazolyl) amino] benzoic acid, 4.5 ml of acetone and 4.5 g (0.045 mole) of triethylamine are placed in a 250 ml flask fitted with an agitator, a thermometer, a condenser and a bromine funnel. A suspension is obtained and 4.90 g (0.045 mole) of ethyl chloroformate is dripped in while the temperature is kept down to 20° C.

The mixture is agitated for 45 minutes at 20° C., then 3.4 g (0.0175 mole) of 1-(1-cyclohexenylmethyl) 2-amino methylpyrrolidine is dripped in, still at 20° C. The reaction is exothermic and cooling is required to keep the mixture at 20° C. It is then agitated for 2 hours at 20° C. and left to stand overnight.

87 ml of soda is added and the acetone and a large part of the water are evaporated under vacuum. A paste is obtained, to which 50 ml of ethanol and 1.5 ml of soda are added. They are heated for 30 minutes under reflux, the ethanol is evaporated under vacuum and 30 ml of water is added. The product crystallizes slowly. It is drained, washed with water and oven-dried at 50° C.

Yield=4.65 g (65%).
Melting point=128° C.
The product is recrystallized in 11.5 ml of 95% ethanol and gives 2 g of crystals melting at 156° C. The NMR spectrum is compatible with the structure of the expected product.

EXAMPLE XI

N-(2-DIETHYLAMINO ETHYL) 2-METHOXY 3-BROMO 4-[(1-H 4,5-DIHYDRO 2-IMIDAZOLYL) AMINO] 5-CHLORO BENZAMIDE

Stage I: METHYL 2-METHOXY 3-BROMO 4-[(1-H 4,5-DIHYDRO 2-IMIDAZOLYL) AMINO] 5-CHLORO BENZOATE 56.7 g (0.2 mole) of methyl 2-methoxy 4-[(1-H 4,5-dihydro 2-imidazolyl) amino] 5-chloro benzoate, 53.5 g (0.3 mole) of N-bromo succinimide, and 100 ml of acetic acid are placed in a 500 ml Erlenmeyer flask. The material is agitated for 2 hours while being heated at 55°–60° C. The solids are dissolved in approximately 15 minutes. The flask is left to stand for 70 hours in an oven at 55°–60° C., then cooled and its contents are stirred into 1 liter of water. The insoluble component is drained and washed. The filtrate is neutralized to pH 6 with soda and simultaneously cooled. 40 g of sodium carbonate is then added in stages to bring the pH to 9-10. The mixture is agitated for half an hour and drained and the precipitate is washed and dried, 60.5 g of crystals with a melting point of 197°–198° C. is obtained. (yield=83.45%).

NMR spectrum: compatible with expected structure.
Br=21.90% (calculated 22.07%).

Stage II: N-(DIETHYLAMINO ETHYL) 2-METHOXY 3-BROMO 4-[(1-H 4,5-DIHYDRO 2-IMIDAZOLYL) AMINO] 5-CHLORO BENZAMIDE 54.38 g (0.15 mole) of methyl 2-methoxy 3-bromo 4-[(1-H 4,5-dihydro 2-imidazolyl) amino] 5-chloro benzoate, 34.8 g (0.3 mole) of diethyl amino ethylamine and 100 ml of ethylene glycol are placed in a 250 ml three-necked flask fitted with an agitator, a thermometer and a reflux condenser. The reactants are agitated for 72 hours at 70° C. then poured into 400 ml of water, and then extracted three times with 200 ml of methylene chloride then with 2×100 ml of the solvent.

The solvent is removed under vacuum and the residue is agitated in 100 ml of isopropyl ether, drained, washed with 50 ml of ether and dried, 33.8 g of product with a melting point of 164° C. is obtained (yield=50%, titer=100.4%). The NMR spectrum is compatible with the expected structure, but the product is nevertheless purified.

33 g of the purified product is then dissolved in 15 volumes of ethyl acetate, treated with black, filtered and crystallized. The product is drained and the mother liquor is concentrated to 3/4, crystallized cold and drained. 25 g of colored material is obtained.

The 25 g of colored material is dissolved in 3 volumes of isopropanol, treated with black, filtered, crystallized at 0° C., drained, washed and dried. This yields 20 g of slightly cream colored material which is again treated with black and crystallized in 3 volumes of isopropanol.

16.3 g of this material is obtained (purification yield=49.4%).

Melting point=179° C., titer=99.5%,
NMR spectrum=compatible.

EXAMPLE XII

N-[(1-BENZYL 2-PYRROLIDINYL) METHYL] 2-METHOXY 4-[(1-H 4,5-DIHYDRO 2-IMIDAZOLYL) AMINO] 5-CHLORO BENZAMIDE 28.35 g (0.10 mole) of methyl 2-methoxy 4-[(1-H 4,5-dihydro 2-imidazolyl) amino] chloro benzoate, 60 ml of methanol and 38 g (0.20 mole) of 1-benzyl 2-aminomethyl pyrrolidine are placed in a 250 ml flask fitted with an agitator, a thermometer and a condenser. The mixture is heated under reflux for about 100 hours and cooled in a bath of ice. The crystals formed are drained, washed three times with 30 ml of methanol and dried overnight in an oven at 50° C.

Yield=36.4 g (82.5%).

Melting point=195° C.

The NMR spectrum reveals the presence of about 30–35 molar % of the initial ester.

The crystals are recovered in 288 ml of absolute ethanol, 38 ml of soda lye is added and the mixture is heated for 2 hours under reflux. 750 ml of water is then added to the suspension and the crystals are drained. The crystals are washed six times with 50 ml of water and dried overnight in an oven at 50° C.

Yield=23 g (52%).

Melting point=210° C.

EXAMPLE XIII

N-(1-ETHYL 2-PYRROLIDINYL METHYL) 2-METHOXY 4-[(1-H 4,5 DIHYDRO 2-IMIDAZOLYL) AMINO] 5 CHLORO BENZAMIDE 28.35 g (0.1 mole) of methyl 2-methoxy 4-[(1-H, 4,5-dihydro 2-imidazolyl) amino] 5-chloro benzoate, 28 ml of ethylene glycol and 14.08 g (0.11 mole) of 1-ethyl 2-aminomethyl pyrrolidine are placed in a 250 ml three-necked flask fitted with an agitator and a thermometer. The reactants are agitated for 48 hours at 70°–75° C. and then cooled. 50 ml of water is added, and the reaction mixture is drained at 20° C., washed with water and dried.

31.3 g (yield: 82.5%) of product is obtained with a melting point of 200° C.

29.6 g of the product is then dissolved in 100 ml of water and 20 ml of concentrated hydrochloric acid, treated with 2.9 g of black, washed with hydrochloric acid, filtered and precipitated with 25 ml of soda lye. The gum is formed into a paste in 150 ml of acetone, agitated, drained, washed with acetone and dried.

24.7 g of product is obtained (yield 83.4%).
Melting Point: 206° C.
NMR: Contains 25% of initial ester.

23.8 g of the product is heated under reflux in 200 ml of water and 9 ml of soda lye, filtered at 60° C., washed with water and dried.

18.9 g is obtained (yield: 79.4%).
Melting point: 222° C.
NMR: Compatible (no ester found).

Purification 18 g of this product is then dissolved cold in 100 ml of water and 12 ml of hydrochloric acid, agitated for one hour with vegetable black, filtered, precipitated by dilute soda lye, drained, washed with acetone and dried.

The 16.4 g of product obtained is dissolved hot in 400 ml of dichloroethane, treated with 3 S ACTI CARBONE black, crystallized cold, drained, washed with dichloroethane and dried at 50° C., then overnight at 100° C.

13 g of product is obtained. (purification yield: 72.3%).

Melting point (Kofler)=222° C.
Titer=98.5%.
Cl=9.39% (calculated 9.33%).
N=18.62% (calculated: 18.44%).
The NMR and IR spectra are compatible.

EXAMPLE XIV

N-(1-CYCLOPROPYLMETHYL 2-PYRROLIDINYL METHYL) 2-METHOXY 4-[(1-H 4,5-DIHYDRO 2-IMIDAZOLYL) AMINO] 5-CHLORO BENZAMIDE 28.35 g (0.1 mole) of methyl 2-methoxy 4-[(1-H, 4,5-dihydro 2-imidazolyl) amino] 5-chloro benzoate, 28 ml of ethylene glycol, and 30.8 g (0.2 mole) of 1-cyclopropylmethyl 2-aminomethyl pyrrolidine are placed in a 250 ml three-necked flask fitted with an agitator and a thermometer. Agitation is carried out for 72 hours at 70°–75° C. The reaction mixture is cooled, 150 ml of water is added and the mixture is drained, washed with water and dried. 33.1 g is obtained (yield: 81.6%) with a melting point of 201° C.

The material is dissolved hot in 150 ml of propanol, two spatulas of black are added, and the mixture is filtered and crystallized cold. It is drained, washed with propanol and dried, to give 27.4 g (crystallization yield: 82.8%).

NMR and IR spectra: Compatible.
Melting point: 198° C.
Titer: 99.8%.
Loss at 100° C.: 0.16%.
Cl: Calculated: 8.73%, found: 8.63%.
N: Calculated: 17.25%, found: 17.56%.

EXAMPLE XV

N-(1-ALLYL 2-PYRROLIDINYL METHYL) 2-METHOXY 4-[(1-H 4,5-DIHYDRO 2-IMIDAZOLYL) AMINO] 5-CHLORO BENZAMIDE 28.35 g (0.1 mole) of methyl 2-methoxy 4-[(1-H, 4,5-dihydro 2-imidazolyl) amino] 5-chloro benzoate, 28 ml of ethylene glycol and 28 g (0.2 mole) of 1-allyl 2-amino methyl pyrrolidine are placed in a 250 ml three-necked flask fitted with an agitator and a thermometer. The mixture is agitated for 72 hours at 70°–75° C.

The reaction mixture is cooled, 150 ml of water is added and the mixture is drained at 10° C., washed with water then acetone (100 ml) and dried. 31.3 g of product is obtained having a melting point of 207° C. The precipitate is resuspended in 200 ml of water and 2 ml of sodium hydroxide. It is heated for 15 minutes to 60°–70° C., filtered hot, washed with water and dried. 31.2 g of product (yield 79.7%) is obtained with a melting point of 207° C.

31 g of this product is then dissolved hot in 200 ml of propanol, treated with 3 S ACTI CARBONE black, filtered, crystallized cold, drained, washed with propanol and dried.

26.7 g of product is obtained (yield 86.1%).
Analysis of product:
Loss of weight at 100° C.: 0.17%.
Melting point (Kofler): 208° C.
Cl: Found: 8.89%; Corrected: 8.90%; Calculated: 9.04%.
N: Found: 18.04%; Corrected: 18.07%; Calculated: 17.87%.
Titer: Found: 99.90%; Corrected: 100.1%.
NMR and IR spectra: Compatible.

EXAMPLE XVI

N-(1-METHYL 2-PYRROLIDINYL METHYL) 2-METHOXY 4-[(1-H 4,5-DIHYDRO 2-IMIDAZOLYL) AMINO] 5-CHLORO BENZAMIDE 28.35 g (0.1 mole) of methyl 2-methoxy 4-[(1-H 4,5-dihydro 2-imidazolyl) amino] 5-chloro benzoate, 28 ml of ethylene glycol and 22.4 g (0.2 mole) of 1-methyl 2-aminomethyl pyrrolidine are placed in a 250 m three-necked flask fitted with an agitator and a thermometer. The mixture is agitated for 72 hours at 70°–75° C. (with an ester not being revealed by NMR).

150 ml of water is then added and the reaction mixture is cooled, drained at 10° C., washed with water then with 100 ml of acetone and dried at 50° C. 32.4 g of product (yield: 88.6%) is obtained with a melting point of 235° C.

32.1 g of this product is then dissolved hot in 400 ml of propanol, treated with black, filtered, crystallized cold, drained, washed with propanol and dried. 27.5 g of crystals is obtained, containing traces of propanol (yield: 85.7%). 25 g of these crystals is dissolved in 250 ml of water and 15 ml of concentrated hydrochloric acid, precipitated by 40 ml of ammonia, drained, washed with water and dried at 60° C.

21.9 g of product is obtained (yield: 87.6%).
Weight loss at 100° C.: 0.3%.
Melting point=236° C. (Kofler).
Titer: Found: 98.5%; Corrected: 98.8%.
Cl: Found: 9.67%; Corrected: 9.70%; Calculated: 9.69%.
N: Found: 19.29%; Corrected: 19.34%; Calculated: 19.14%.

The NMR and IR spectra are compatible with the proposed structure.

EXAMPLE XVII

N-(1-PROPYL 2-PYRROLIDINYL METHYL) 2-METHOXY 4-[(1-H 4,5-DIHYDRO 2-IMIDAZOLYL) AMINO] 5-CHLORO BENZAMIDE

Following the same procedure in Example XV, 28.5 g (0.1 mole) of methyl 2-methyl 4-[(1-H 4,5-dihydro 2-imidazolyl) amino] 5-chloro benzoate and 28.4 g (0.2 mole) of 1-propyl 2-aminomethyl pyrrolidine are reacted in 28 ml of ethylene glycol. 34.2 g of product (yield: 86.9%) is obtained having a melting point of 207° C. 34 g of this product is then dissolved hot in 300 ml of propanol, treated with 3 S ACTI CARBONE black, filtered, recrystallized cold, drained, washed with propanol and dried.

29.6 g of product is obtained (yield: 87%).
Weight loss at 100° C.: 0.12%.
Melting point=207° C. (Kofler).
Cl: Found: 8.88%; Corrected: 8.89%; Calculated: 9.00%.
N: Found: 18.01%; Corrected: 18.0.3%; Calculated: 17.78%.
Titer: Found: 99.7%; Corrected: 99.8%.
NMR and IR spectra: compatible with the expected structure.

EXAMPLE XVIII

N-(DIETHYAMINO ETHYL) 2-METHOXY 4-[(1-H 4,5-DIHYDRO 2-IMIDAZOLYL AMINO] 5-BROMO BENZAMIDE 24.6 g (0.075 mole) of methyl 2-methoxy 4-[1-H 4,5-dihydro 2-imidazolyl) amino] 5-bromo benzoate, 40 ml of ethylene glycol and 17.4 g (0.15 mole) of diethyl amino ethylamine are placed in a 250 ml three-necked flask fitted with an agitator and a thermometer. The mixture is agitated for 72 hours at 70°–75° C. 80 ml of water is added and the reaction mixture is cooled, drained at 10° C. and washed with water. The precipitate is recovered in 100 ml of water with 0.8 g of sodium hydroxide, agitated for 15 minutes at 70°–80° C., filtered hot, washed with water then acetone and dried at 50° C.

26.4 g of product is obtained (yield 85.4%), with melting point of 216° C. (Titer=99.5%, NMR is compatible with expected structure.

25.8 g of this product is then dissolved in 390 ml (15 volumes) of isopropanol, treated with 3 S ACTI CARBONE black, crystallized cold, drained, washed with acetone and dried.

23.3 g is obtained (purification yield 86.7%).
Analysis of Product:
Melting Point (Kofler) 217° C.
Weight loss at 100° C. 0.01%.
Titer 98.8%.
Br 19.61% (calculated 19.40%).
N 17.04% (calculated 16.98%).
NMR and IR spectra compatible.

EXAMPLE XIX

N-(1-ETHYL 2-PYRROLIDINYL METHYL) 2-METHOXY 4-[(1-H 4,5-DIHYDRO 2-IMIDAZOLYL) AMINO] 5-BROMO BENZAMIDE 24.6 g (0.075 mole) of methyl 2-methoxy 4-[(1-H 4,5-dihydro 2-imidazolyl amino] 5-bromo benzoate and 19 g (0.15 mole) of 1-ethyl 2-aminomethyl pyrrolidine are reacted in 40 ml of ethylene glycol, following the procedure described in Example XVII exactly. 28.72 g (yield 90.5%) of crystals is obtained, melting point 235° C. (Titer 98.8%). NMR is compatible with expected structure. 27.65 g of the product is dissolved hot in 10 volumes of propanol, treated with 3 S ACTI CARBON black, filtered, crystallized cold, drained, washed with acetone and dried. 24 g is obtained (yield: 87%).
Analysis of Product:

NMR compatible.
Loss at 100° C. 0.33%.
Melting point (Kofler) 237° C.
Br Found: 18.61%; Corrected: 18.67%; Calculated: 18.84%.
N Found: 16.48%; Corrected: 18.0%; Calculated: 18.50%.
Titer Found: 98.1%; Corrected: 98.4%.

EXAMPLE XX

N-(1-ALLYL 2-PYRROLIDINYL METHYL) 2-METHOXY 4-[(1-H 4,5-DIHYDRO 2-IMIDAZOLYL) AMINO] 5-BROMO BENZAMIDE 24.6 g (0.075 mole) of methyl 2-methoxy 4-[(1-H 4,5-dihydro 2-imidaolyl) amino] 5-bromo benzoate and 21 g (0.15 mole) of 1-allyl 2-amino methyl pyrrolidine are reacted in 40 ml of ethylene glycol, following the procedure described in Example XVII exactly. 28.46 g of material with a melting point of 214° C. is obtained (yield=87%; titer 99.1%). NMR is compatible with expected structure.

27.45 g of product is dissolved hot in 11 volumes of propanol, treated with 3 S ACTI CARBONE black, filtered, crystallized cold, drained, washed with propanol and dried. 24.85 g of product is obtained (purification yield: 90.5%).

Analysis of Product:
Melting point (Kofler)=215° C.
Weight loss (100° C.)=0.13%.
Titer Found=98.6%; Corrected=98.7%.
Br Found=18.4%; Corrected=18.49%; Calculated=18.33%.
N Found=16.11%; Corrected=16.13%; Calculated=16.05%.
NMR and IR spectra are compatible.

EXAMPLE XXI

N-(2-DIETHYLAMINOETHYL) 2-METHOXY 4-[(1-H 4,5DIHYDRO 4-METHYL 2-IMIDAZOLYL AMINO] 5-CHLORO BENZAMIDE

Stage 1: METHYL 2-METHOXY 4-(N'2-AMINO] 1(or 2)-ISOPROPYL) THIOUREIDO 5-CHLORO BENZOATE 51 ml (0.60 mole) of 1,2-diamino propane and 200 ml of isopropyl ether are placed in a 1 liter three-necked flask fitted with an agitator, a thermometer and a filling funnel. The mixture is cooled to 0°, −5° C. and a solution of 39.9 g (0.12 mole) of methyl 2-methoxy 4-isothiocyanato 5-chloro benzoate in toluene is poured in during the course of half an hour. Agitation is continued for 10 minutes and the solvents are drawn off. The medium is then agitated with 850 ml of water, and gum-like material crystallizes. The precipitate is drained, washed with water and dried overnight under vacuum.

40.2 g is obtained. (Yield: 60.6%).
Melting point=100°–105° C.
NMR=Compatible with a 40–60% mixture of the two isomers.

Stage II: METHYL 2-METHOXY 4-[(1-H 4,5-DIHYDRO 4-METHYL 2-IMIDAZOLYL) AMINO] 5-CHLORO BENZOATE 39.9 g (0.12 mole) of methyl 2-methoxy 4-(N'2-amino 1-(or 2) isopropyl) thioureido 5-chloro benzoate is placed in a three-necked flask with 90 ml of water and heated to 70°–75° C. A solution of 40.6 g (0.15 mole) of lead acetate in 160 ml of distilled water is poured in at that temperature in the course of 30 minutes. The mixture is agitated for ¾ hour at 70°–75° C. and cooled to 20° C. The lead sulphide is drained and washed. A solution of 27.3 g of sodium carbonate (0.26 mole) in 200 ml of water is prepared and half of it is added to the previous filtrate. The lead salts are precipitated and are drained and washed. The filtrate is made alkaline with the remainder of the sodium carbonate solution. The precipitate formed is drained, washed with water and dried under vacuum at 25° C.

26.5 g is obtained (yield: 66.4%).
Melting point: melting complete at 140° C.
Titer: 98.8%.
NMR: Compatible.

Stage III: N-(2-DIETHYLAMINOETHYL) 2-METHOXY 4-[(1-H 4,5-DIHYDRO 4-METHYL 2-IMIDAZOLYL) AMINO] 5-CHLORO BENZAMIDE 29.75 g (0.1 mole) of methyl 2-methoxy 4-[(1-H 4,5-dihydro 4-methyl 2-imidazolyl) amino] 5-chloro benzoate, 30 ml of ethylene glycol and 23.2 g (0.2 mole) of diethylamino ethylamine are placed in 250 ml three-necked flask and agitated for 72 hours at 70°–75° C. 150 ml of water is added and the mixture is cooled to 15° C., drained, washed with water and acetone and dried at 50° C.

33.4 g is obtained (yield: 87.5%).
Melting point=179° C.
NMR=Ester not found—compatible.

The material is dissolved hot in 200 ml of ethanol, treated with black, filtered, recrystallized cold, drained, washed with ethanol and dried at 60° C.

23.5 g is obtained (purification yield: 70.4%).
Melting point (Kofler)=185° C.
Weight loss (100° C.)=0.09%.
Titer=99.5%.
Cl=9.19% (calculated: 9.28%).
N=18.37% (calculated: 18.34%).

The NMR and IR spectra are compatible with the structure proposed.

EXAMPLE XXII

N-(1-ETHYL 2-PYRROLIDINYL METHYL) 2-METHOXY 4[(1-H 4,5-DIHYDRO 4-METHYL 2-IMIDAZOLYL) AMINO] 5-CHLORO BENZAMIDE 29.75 g (0.1 mole) of methyl 2-methoxy 4-[(1-H 4,5-dihydro 4-methyl 2-imidazolyl) amino] 5-chloro benzoate, 30 ml of ethylene glycol and 25.6 g (0.2 mole) of 1-ethyl 2-aminomethyl pyrrolidine are placed in a 250 ml three-necked flask. The mixture is agitated for 72 hours at 70°–75° C. and 150 ml of water is added. The mixture is cooled, drained, washed with water and acetone (material is slightly soluble in acetone) and dried at 50° C.

24.6 g of the product, which melts at 180° C. is obtained.
(yield=62.5%).
NMR: compatible with expected structure.

The material is solubilized hot in 150 ml of isopropanol, treated with black, filered hot, crystallized cold, drained, washed and dried at 70° C. 13.2 g of crystals is obtained.

Melting point (Kofler) 166° C., recrystallizes and melts again at 180° C. Loss at 100° C. is 0.43%.

|  | Found | Corrected | Calculated |
|---|---|---|---|
| Titer % | 98.5 | 98.9 |  |
| N % | 17.49 | 17.56 | 17.78 |
| Cl % | 8.97 | 9.01 | 9.00 |

The NMR and IR spectra are compatible with the structure proposed.

EXAMPLE XXIII

N-(1-ALLYL 2-PYRROLIDINYL METHYL) 2-METHOXY 4-[(1-H 4,5-DIHYDRO 4-METHYL 2-IMIDAZOLYL) AMINO] 5-CHLORO BENZAMIDE 29.75 g (0.1 mole) of methyl 2-methoxy 4-[1-H 4,5-dihydro 4-methyl 2-imidazolyl) amino] 5-chloro benzoate, 30 ml of ethylene glycol and 28 g (0.2 mole) of 1-allyl 2-amino methyl pyrrolidine are placed in a 250 ml three-necked flask. The mixture is agitated at 70°–75° C. for 72 hours and 100 ml of water added. The mixture is cooled to 15° C., drained, washed with water then acetone and dried at 50° C. 32.6 g of material is obtained (yield: 80.4%).

The product is dissolved hot in 200 ml of absolute ethanol, treated with 3 S ACTI CARBONE black, filtered, recrystallized cold, drained, washed with ethanol and dried at 60° C.

21.3 g is obtained (purification yield: 65.3%).
Melting point (Kofler): 170° C.
Weight loss at 100° C.: 0.1%.
Titer: 100.7%.
Cl: 8.52% (calculated: 8.73%).
N: 17.48% (calculated: 17.25%).
NMR and IR spectra compatible with proposed structure.

EXAMPLE XXIV

N (DIETHYLAMINOETHYL) 2-METHOXY 4-[(1-H 4,5-DIHYDRO 4-METHYL 2-IMIDAZOLYL) AMINO] 5-BROMO BENZAMIDE

Stage I: METHYL 2-METHOXY 4-(N'2-AMINO 1-(or 2) ISOPROPYL) THIOUREIDO 5-BROMO BENZOATE 51 ml (0.6 mole) of 1,2 diaminopropane and 200 ml of isopropyl ether are placed in a 2 liter three-necked flask fitted with an agitator, a thermometer and a filling funnel. The mixture is cooled to 0° C., −5° C. and 60.4 g of (0.2 mole) of a solution of methyl 2-methoxy 4-isothiocyanato 5-bromo benzoate in 350 ml of toluene is dripped over the course of one hour. When all of the solution has been added, at 0° C., −5° C., the thiourea adheres to the walls. The solvent is drawn off, 500 ml of water is added and the mixture is agitated for 15 minutes. It crystallizes, is drained, washed with water and dried overnight at 30° C. under vacuum.

58.8 g of product is obtained (yield=78.2%).
Melting point: 117° C.
Titer: 101.9%.
NMR: Compatible with a mixture of the isomers (60%–40%).

Stage II: METHYL 2-METHOXY 4-[(1-H 4,5-DIHYDRO 4-METHYL 2-IMIDAZOLYL) AMINO] 5-BROMO BENZOATE 310.6 g (0.826 mole) of methyl 2-methoxy 4-(N'2-amino 1-(or 2) isopropyl) thioureido 5-bromo benzoate and 1.250 liter of chlorobenzene are placed in a two liter three-necked flask fitted with an agitator, a thermometer and a condenser. The mixture is heated for 5 hours at 100° C. with agitation then cooled to 15° C. and drained. The precipitate is washed with isopropyl ether and dried at 70° C. 220.4 g of product is obtained with a melting point that is not clearly defined (from 145° C.).

219 g of this material is dissolved under reflux in 900 ml of a 40% solution of isopropanol in water, treated with 3 S ACTI CARBONE black, filtered and crystallized in situ. It is filtered, washed with a chilled aqueous solution of isopropanol and dried at 70° C.

169.5 g is obtained (purification yield 77.4%.
Melting point: 168° C.
Titer: 98.2%.
NMR: Compatible, there are still traces of chlorobenzene and isopropanol.

Stage III: N-(DIETHYLAMINO ETHYL) 2-METHOXY 4-[(1-H 4,5-DIHYDRO 4-METHYL 2-IMIDAZOLYL) AMINO] 5-BROMO BENZAMIDE 34.2 g (0.1 mole) of methyl 2-methoxy 4-[(1-H 4,5-dihydro 4-methyl 2-imidazolyl) amino] 5-bromo benzoate, 60 ml of ethylene glycol and 23.2 g (0.2 mole) of diethylamino ethyl amine are placed in a 250 ml three-necked flask and agitated for 72 hours at 70°–75° C. 100 ml of water is added and the mixture is cooled to 10° C., drained, washed with water then petroleum ether and dried.

40.4 g is obtained (yield=95%).
Melting point: 203° C.
Titer: 98.5%.
NMR: Compatible with expected structure.

39.7 g of the product is dissolved hot in 6 volumes (240 ml) of absolute ethanol, treated with black, filtered, crystallized cold, drained, washed with isopropyl ether and dried at 60° C.

34.6 g is obtained (purification yield: 87.3%).
Melting point (Kofler): 198° C.
Loss at 100° C.: 0.04%.
Titer: 98.9%.
N: 16.31% (calculated 16.43%).
Br: 19.17% (calculated 18.76%).
The NMR and IR spectra are compatible with the structure proposed.

EXAMPLE XXV

N (1-ETHYL 2-PYRROLIDINYL METHYL) 2-METHOXY 4-[(1-H 4,5-DIHYDRO 4-METHYL 2-IMIDAZOLYL) AMINO] 5-BROMO BENZAMIDE 34.2 g (0.1 mole) of methyl 2-methoxy 4-[(1-H 4,5-dihydro 4-methyl 2-imidazolyl) amino] 5-bromo benzoate, 60 ml of ethylene glycol and 25.6 g (0.2 mole) of 1-ethyl 2-amino methyl pyrrolidine are placed in a 250 ml three-necked flask and agitated continuously for 72 hours at 70°–75° C. 100 ml of water is added and the reaction mixture is cooled to 10° C., drained, washed with water then acetone and dried.

37.3 g is obtained (yield: 85.4%).

Melting point: 200° C. (with particles melting at 190° C.).

Titer: 98%.

NMR: Compatible with expected structure.

36.6 g of the product is dissolved hot in 270 ml of absolute ethanol, treated with black, filtered, crystallized cold, drained, washed with isopropyl ether and dried.

This gives: 25.6 g (purification yield: 70%).

Kofler M P: About 170° C., recrystallizes and melts again at 196° C.

Loss at 100: 0.56%.

Titer—Found: 98.6%—Corrected: 99.2%.

N Found: 15.70%—Corrected: 15.79%—Calculated: 15.98%

Br Found: 18.01—Corrected: 18.11%—Calculated: 18.25%

The NMR and IR spectra are compatible with the structure proposed.

EXAMPLE XXVI

N-(1-ALLYL 2-PYRROLIDINYL METHYL) 2-METHOXY 4-[(1-H 4,5-DIHYDRO 4-METHYL 2-IMIDAZOLYL) AMINO] 5-BROMO BENZAMIDE 34.2 g (0.1 mole) of methyl 2-methoxy 4-[(1-H 4,5-dihydro 4-methyl 2-imidazolyl) amino] 5-bromo benzoate is reacted with 28 g (0.2 mole) of 1-allyl 2-aminomethyl pyrrolidine in 60 ml of ethylene glycol, following the same procedure as in Example 25.

40.17 g is obtained (yield: 89.4%).

Melting point: 175° C.

Titer: 97%.

NMR: Compatible with expected structure.

40 g is dissolved hot in 200 ml of ethanol, treated with 3 S ACTI CARBONE black, filtered, crystallized cold, drained, washed with isopropyl ether and dried.

This gives: 31.37 g (purification yield: 78.5%).

Melting point (Kofler): 174° C.

Loss at 100° C.: 0.09%.

Titer: 99.1%.

N: 15.35% (calculated: 15.55%).

Br: 18.13% (calculated: 17.76%).

The NMR and IR spectra are compatible with proposed structure.

EXAMPLE XXVII

N (DIETHYLAMINO ETHYL ) 2-METHOXY 4-[(1-H 4,5-DIHYDRO 4-DIMETHYL 2-IMIDAZOLYL) AMINO] 5-CHLORO BENZAMIDE

Stage I: METHYL 4-[N'(2-METHYL 2-AMINO PROPYL) THIOUREIDO] 5-CHLORO BENZOATE 400 ml of isopropyl ether and 83.6 ml (0.8 mole) of 1,2-diamino 2-methyl propane are placed in a 2 liter three-necked flask fitted with an agitator, a thermometer and a filling funnel. They are cooled to 0°, −5° C. and a solution of 103 g (0.4 mole) of methyl 2-methoxy 4-isothiocyanato 5-chloro benzoate in 600 ml of toluene is poured in in the course of 45 minutes, with the temperature being kept at that level. The reaction mixture is agitated for a further 15 minutes and the solvents are drawn off. The gum-like substance stuck to the walls is crystallized by agitating it in one liter of water.

It is left to stand overnight, drained, washed with water and dried.

117.7 g is obtained (yield 85.2%).

Melting point 149°–150° C.

NMR compatible (no isomers can be distinguished).

Stage II: METHYL 2-METHOXY 4-[(1-H 4,5-DIHYDRO 4-DIMETHYL 2-IMIDAZOLYL) AMINO] 5-CHLORO BENZOATE 117.7 g (0.34 mole) of methyl 2-methoxy 4-[N'-(2-amino 2-methyl propyl) thioureido] 5-chloro benzoate in 470 ml of chlorobenzene is placed in a 2 liter three-necked flask and heated to 100° C. with agitation for 5 hours. The solids are completely dissolved at about 85°–90° C. The solution is cooled to 20° C. and 470 ml of water and 50 ml of acetic acid are added.

The reaction mixture is decanted, the organic phase is washed with 250 ml of water and the aqueous portions are made alkaline with 106 g of sodium carbonate (pH 10). A slowly crystallizing paste forms. The product is drained, washed with water and dried to give 90.1 g (yield=85.1%) of crystals which melt at from 130° to 180° C., 109.4 g of the product is dissolved hot in 440 ml of ethanol, treated with black, filtered, crystallized cold, drained, washed with ethanol and dried.

88 g of product is obtained (yield=80.4%).

Melting point=167° C.

Titer=94.3%.

NMR compatible (solvents present).

Stage III: N(DIETHYLAMINO ETHYL) 2-METHOXY 4-[(1-H 4,5-DIHYDRO 4-DIMETHYL 2-IMIDAZOLYL) AMINO] 5-CHLORO BENZAMIDE 31.15 g (0.1 mole) of methyl 2-methoxy 4-[(1-H 4,5 dihydro 4-dimethyl 2-imidazolyl) amino] 5-chloro benzoate, 35 ml of ethylene glycol and 23.2 g (0.2 mole) of diethylamino ethyl amine are placed in a 250 ml three-necked flask fitted with an agitator and a thermometer and are agitated for 80 hours at 70°–75° C. 150 ml of water is then added and the reaction mixture is cooled, drained, washed with water than acetone and dried at 50° C. 33.4 g is obtained (yield=84.45%) with a melting point of 194° C.

33.4 g of this product is dissolved hot in 200 ml of a 50—50 isopropanol-water solution, treated with 3 S ACTICARBONE black, filtered, crystallized cold, drained, washed with a 50—50 isopropanol-water solution and dried for one night at 60° C. then one night at 70° C.

26 g of the product is obtained (purification yield 77.8%).

Kofler melting point 189° C.

Loss at 100° C. 0.06%.

Titer 98.1%.

Cl 9.02% calculated 8.95%.

N 17.67% calculated 17.69%.

The NMR and IR spectra are compatible.

EXAMPLE XXVIII

N-(1-ALLYL 2-PYRROLIDINYL METHYL) 2-METHOXY 4-[(1-H 4,5-DIHYDRO 4-DIMETHYL 2-IMIDAZOLYL) AMINO] 5-CHLORO BENZAMIDE 31.15 g (0.1 mole) of methyl 2-methoxy 4-[(1-H 4,5-dihydro 4-dimethyl 2-imidazolyl) amino] 5-chloro benzoate, 35 ml of ethylene glycol and 28 g (0.2 mole) of 1-allyl 2-aminomethyl pyrrolidine are placed in a 250 ml three-necked flask fitted with an agitator, a thermometer and a condenser and agitated for 80 hours at 70°–75° C. (NMR no longer reveals any ester). 150 ml of water is added and the reaction mixture is cooled to 5° C., drained, washed with water then acetone and dried. 26.7 g is obtained (yield 63.6%) (Melting point=160° C.).

26.7 g of the product is dissolved hot in 265 ml of ethyl acetate, treated with 3 S ACTICARBONE black, filtered, crystallized cold, drained, washed with ethyl acetate and dried at 50° C.

18.9 g is obtained (purification yield=70.8%).
Kofler melting point 161° C.
Loss at 100° C. 0%.
Titer 98.4%.
Cl 8.41% (calculated 8.44%).
N 16:45% (calculated 16.68%).
The NMR and IR spectra are compatible.

EXAMPLE XXIX

N-(DIETHYL AMINO ETHYL) 2-METHOXY [(1,4-DIHYDRO 2-IMIDAZOLYL) AMINO] 5-CHLORO BENZAMIDE

Stage I: 2-CHLORO 4-(DIETHYLAMINO 2-ETHYLAMINO CARBONYL) 5-METHOXY PHENYL SODIUM DITHIOCARBAMATE 600 g of N(diethylaminoethyl) 2-methoxy-4-amino 5-chloro benzamide in 2.4 l of tetrahydrofuran is placed in a 6 liter three-necked flask fitted with an agitator, a thermometer, a reflux condenser and a filling funnel. 144 g of 50% sodium hydroxide is added in stages in the course of 20 minutes at approximately 25°–30° C. The mixture is heated for 2 hours under reflux and cooled to 20° C. 400 ml of carbon sulphide is introduced in a thin stream (taking 20 minutes) with vigorous agitation. The mixture is heated slowly to 50° C. and a slight reflux is maintained for 30 minutes, then agitation and heating are stopped and the material is left to stand overnight. It is drained, washed twice with 1.5 liter of chloroform and dried in air then in an oven at 50° C.

886 g is obtained (yield=111%).

NMR compatible, small amount of impurity, none of initial benzamide.

Stage II: N-(DIETHYLAMINOETHYL) 2-METHOXY-4-ISOTHIOCYANATO 5-CHLORO BENZAMIDE 159 g of sodium 2-chloro 4-(diethylamino 2-ethylaminocarbonyl)-5-methoxy phenyl dithiocarbamate in 470 ml of ethyl ether is placed in a one liter three-necked flask fitted with an agitator, a thermometer, a condenser and a filling funnel. It is cooled and 43.4 g of ethyl chloroformate is poured in at 20° to 22° C. in the course of 30 minutes. The physical appearance of the suspended crystals changes. Agitation is continued for 2 hours at 20° C. The material is drained and the suspended precipitate is recovered in 150 ml of water, redrained, washed with water and oven-dried at 50° C.

87 g of product is obtained (Melting point 100° to 150° C.).

Yield=63.7%.

NMR compatible, no N-(diethylamino ethyl) 2-methoxy 4-amino 5-chlorobenzamide base detected.

Stage III: N-(DIETHYLAMINO ETHYL) 2-METHOXY 4-[1,4-DIHYDRO 2-IMIDAZOLYL) AMINO] 5-CHLORO BENZAMIDE 105 g of N-(diethylaminoethyl) 2-methoxy 4-isothiocyanato-5-chloro benzamide in 1 liter of xylene is placed in a 2 liter three-necked flask fitted with an agitator, a thermometer, a reflux condenser and a filling funnel. 30 g of ethylene diamine is poured in in a thin stream while the temperature is kept down to no more than 25° C. (taking 15 minutes).

There is a marked thickening of the material. It is agitated for 2 hours at room temperature. The material is brought to reflux and kept under reflux for 10 hours. The temperature rises to 125°–128° C. The insoluble component is filtered off hot and the filtrate is cooled to 10° C. The precipitate is drained and washed with water (about 400 cc). It is oven-dried at 50° C. This gives 75 g of a product containing about 30 to 35% of the N(diethylamino ethyl) 2-methoxy 4-amino 5-chloro benzamide base. The melting point is pasty from 140° C.

The product is agitated for 1 hour in 75 ml of chloroform, drained and dried. This gives 55 g of a product (melting point=185° C.) still containing 5 to 10% of the N(diethylamino ethyl) 2-methoxy 4-amino 5-chloro benzamide base. When this product has been recrystallized in 400 ml of ethanol and an insoluble substance filtered off hot, 36 g of product is obtained.

(Melting point 197° C.—NMR: Compatible—no impurities detected).

By concentrating the filtrates to 50 ml a second run of 8 g is obtained (melting point 192° C.) containing very little impurity.

There is a total yield of 40%.
Analysis of Product:
Titer % 98.6.
Cl % 8.83 (theory 9.64).
$H_2O$ % >0.1.

EXAMPLE XXX

N-(1-CYCLOPENTYL 2-PYRROLIDINYL METHYL) 2-METHOXY 4-[(1-H 4,5-DIHYDRO 2-IMIDAZOLYL) AMINO] 5-CHLORO BENZAMIDE 28.35 g (0.1 mole) of methyl 2-methoxy 4-[(1-H 4-5 dihydro 2-imidazolyl) amino] 5 chloro benzoate, 60 ml of ethylene glycol and 33.6 g (0.2 mole) of 1-cyclopentyl 2-aminomethyl pyrrolidine are placed in a 250 ml three-necked flask fitted with an agitator, a thermometer and a condenser, and agitated for 72 hours at 75° C. The medium is cooled; 100 ml of water is added and agitated for 15 minutes, drained, washed four times with acetone and dried. A yield of 33.7 g (yield: 80.3%) with a melting point of 166° C. NMR: Compatible (no ester detected).

33 g of the product is recrystallized isopropanol and treated with black. The precipitate is drained, washed with isopropanol and dried. 26 g of product is obtained. A 10% aqueous hydrochloride solution is colored.

23.8 g of the product is recovered in 238 ml of water and 6.5 ml of acetic acid, treated with black, filtered, precipitated by 20 ml of ammonia, drained, washed with water and dried at 70° C. under vacuum over phosphoric anhydride. 20.5 g of produce is obtained (purification yield=67.8%), melting at 206° C. (NMR and IR spectra compatible with expected structure).

Titer: 98.2%—Corrected: 99.8%.

Cl: 8.25%—Corrected: 8.39—Calculated: 8.44%.
H$_2$O: 1.6%.

EXAMPLE XXXI

N-[(1-(2-CYCLOHEXENYL) 2-PYRROLIDINYL) METHYL] 2-METHOXY 4-[(1-H 4,5-DIHYDRO 2-IMIDAZOLYL) AMINO] 5-CHLORO BENZAMIDE 36.8 g (0.130 mole) of methyl 2-methoxy 4 [(1-H 4,5-dihydro 2-imidazolyl) amino] 5-chloro benzoate, 73 ml of methanol, 46.8 g (0.260 mole) of 1-(2-cyclohexen-1-yl) 2-aminomethyl pyrrolidine and 3 drops of hydrochloric acid (d=1.18) are placed in a 250 ml flask fitted with an agitator, a thermometer and a condenser. The suspension is heated under reflux for 70 hours. The ester gradually becomes soluble. It is cooled to 20° C., slightly insoluble material is filtered off, the filtrate is evaporated dry under vacuum and 200 ml of water is added to the pasty residue. The product crystallizes. It is drained, washed with plenty of water (6×80 ml of water) and oven-dried at 50° C. for two days. The filtrate is found to contain an insoluble oil. A yield of 45.6 g (81%) is obtained with a melting point=186° C.

The product is recrystallized in 250 ml of 95% ethanol. It is drained, washed twice with a small amount of alcohol then oven-dried overnight at 50° C. (Slight surface yellowing).
Yield=35.4 g (63%).
Melting point=204° C.

The NMR and IR spectra are compatible with the structure of the expected product.

EXAMPLE XXXII

N (2-PYRROLIDINYL METHYL) 2-METHOXY 4-[(1-H 4,5-DIHYDRO 2-IMIDAZOLYL) AMINO] 5-CHLORO BENZAMIDE 141 g (0.5 mole) of methyl 2-methoxy 4-[(1-H 4,5-dihydro 2-imidazolyl) amino] 5-chloro benzoate, 250 ml of ethylene glycol and 100 g (1 mole) of 2-aminomethyl pyrrolidine are placed in a three-necked flask fitted with an agitator, a thermometer and a reflux condenser. They are agitated at 70° C. for 72 hours. The material is cooled and poured into 1.5 liters of chilled water. The suspension is agitated for 1 hour, drained, washed in water and dried.

107.2 g of product is obtained.
Yield: 60.9%.
Melting point: 195° C.
NMR compatible but impure.

The filtrate is extracted with 2×500 ml of methylene chloride, the solvent is removed dry under vacuum and the residue is recovered with 100 ml of water. The suspension is agitated for 2 hours, drained, washed and dried.

8.5 g is obtained (4.85%).
Melting point: 188°–190° C.
NMR compatible but impure.

120 g of product is recrystallized in 360 ml of propanol, treated with black, chilled, drained, washed with 50 ml of acetone and dried. 90 g is obtained. The filtrate is concentrated to give a second run of 20 g. The 110 g is suspended in 0.5 liter of water and acidified with hydrochloric acid until it dissolves. It is then treated with black, filtered, made alkaline by 10% sodium hydroxide, drained, washed and dried. 55 g is obtained. NMR is compatible.

30.8 g of the product is dissolved in 118 ml of distilled water and 189.13 ml of hydrochloric acid. When the solution has been treated with black it is filtered and made alkaline by a solution of 21 ml of 10N sodium hydroxide and 20 ml of water. The suspension is agitated for 15 minutes and the precipitate is drained, washed with plenty of water and dried at 60° C. under vacuum over P$_2$O$_5$, for four days.

25.5 g of product is obtained.
Analysis of Product:
Melting point 206° C.
H$_2$O 1.3%.
Titer (corrected): 100.9%.
Cl (corrected): 9.92% (calculated 10.07%).
NMR and IR spectra compatible with proposed structure.

EXAMPLE XXXIII

N-(DIETHYLAMINO ETHYL) 2-ALLYLOXY 4-[(1-H 4,5 DIHYDRO 2-IMIDAZOLYL) AMINO] 5-CHLORO BENZAMIDE

Stage I: ETHYL 2-HYDROXY 4-ACETAMINO 5-CHLORO BENZOATE 430 g of methyl 2-hydroxy 4-acetamino benzoate and 2,150 g of acetic acid are placed in a 4 liter flask fitted with an agitator, a thermometer and a condenser, and heated to approximately 35°–40° C. before 278 g of N-chloro succinimide is added. The temperature is kept at 40° C. until all the solids have dissolved, then raised to 50° C. for 23 hours. Crystals appeared thereafter. The reaction mixture is cooled to 20° C. and poured into a 20 liter reactor containing 2 kg of ice. The precipitate which formed is drained, washed with water and oven-dried at 50° C.
Yield=483.5 g (96%).
Melting point=150°–154° C.

Stage II: METHYL 2-ALLYLOXY 4-ACETAMINO 5-CHLORO BENZOATE 428 g of methyl 2-hydroxy 4-acetamino 5-chloro benzoate, 1,990 g of dimethylformamide, 8.8 g of benzyltributylammonium chloride, 266.6 g of potassium carbonate and 164 g of allyl chloride are placed in a 4 liter flask fitted with an agitator, a thermometer and a condenser.

The reaction mixture is heated for one hour at 50° C., one hour at 60° C., one hour at 70° C. and one hour at 80° C. The mixture is cooled to 20° C. and the contents of the flask are poured into a reactor containing 2 kg of ice and 2,385 ml of water. The precipitate which formed was drained, washed with water and oven-dried at 50° C.
Yield=463 g (93%).
Melting point=104°–106° C.

The product is purified by recrystallizing it in 1,200 ml of toluene.
Yield=294 g (59%).
Melting point=111°–112° C.

Stage III: METHYL 2-ALLYLOXY 4-AMINO 5-CHLORO BENZOATE 293.5 g of methyl 2-allyloxy 4-acetamino 5-chloro benzoate and 1,426 ml of methanol are placed in a 3 liter flask fitted with an agitator, a thermometer, a condenser and a bromine funnel. Then, 108 g of sulphuric acid (d=1.83) is added in a thin stream and the temperature is allowed to rise. The materials are then heated under reflux for 1.5 hours, cooled to 20° C. and the contents of the flask are then poured into a reactor containing 1300 g of ice and 5000 ml of water. The reactor contents are agitated for one hour. A precipitate which forms is drained, washed with water and oven-dried at 60° C.

Yield=241 g (96%).
Melting point=110° C.

Stage IV: METHYL 2-ALLYLOXY 4-ISOTHIOCYANATO 5-CHLORO BENZOATE 241 g of methyl 2-allyloxy 4-amino 5-chloro benzoate, 116 g of potassium carbonate and 1345 g of 1,2-dichloroethane are placed in a 2 liter flask fitted with an agitator, a thermometer, a condenser and a bromine funnel and 148 g of thiophosgene is dripped in at 20° C.

The reactants are heated for 2 hours at 50°-60° C., then 2 hours at 70°-80° C., after which they are cooled to 20° C. The salts are filtered and washed with a small quantity of dichloroethane and the filtrate is evaporated under vacuum at 50° C. The pasty residue is placed in a beaker and dissolved in 500 ml of petroleum ether.

Very hard crystals and lumps form. They are left to stand overnight at about 0°-5° C., then the solid is drained, washed with a small quantity of petroleum ether and dried in air.

Yield=240 g (85%).
Melting point=74°-75° C.

Stage V: METHYL 2-ALLYLOXY 4-[(1-H 4,5-DIHYDRO 2-IMIDAZOLYL) AMINO] 5-CHLORO BENZOATE 152 g of ethylenediamine and 845 ml of methylene chloride are placed in 4 liter flask fitted with an agitator, a thermometer, a condenser and a bromine funnel. A solution of 240 g of methyl 2-allyloxy 4-isothiocyanato 5-chloro benzoate in 1270 ml of methylene chloride is added in a thin stream at 20° C. The contents are agitated for 30 minutes at 20° C. and then 845 ml of water is added. The mixture is agitated for one hour and the organic phase, decanted. The organic phase is washed twice with 850 ml of water and the solvent is evaporated under vacuum.

A very thick yellow oil is obtained. 1690 ml of ethanol is added, the mixture is heated to about 30°-35° C. until all the solids have dissolved, then 400 ml of solvent is evaporated under vacuum. The solution is heated to 60° C. and a solution of 338 g of trihydrated lead acetate in 1350 ml of water is poured in through a bromine funnel. The mixture is heated for 2 hours under reflux and cooled. The black precipitate which forms is filtered off at about 70° C.

The filtrate is washed with ethanol and acidified with 17 ml of sulphuric acid (d=1.83) in solution in 212 ml of water, when the temperature has been reduced to 20° C. 1500 ml of water is added, 1400 ml of ethanol is evaporated under vacuum (bath at 60° C.) and the material is left to stand overnight at 20° C. Thereafter it is filtered in the presence of 3 S carbon black, and the filtrate made alkaline with 211 ml of ammonia (d=0.90).

The product crystallizes and is filtered, washed with water and oven-dried at 50°-60° C.

Yield=215 g (82%).
Melting point=174°-178° C.

Stage VI: N-(DIETHYLAMINO ETHYL) 2-ALLYLOXY 4-[(1-H 4,5-DIHYDRO 2-IMIDAZOLYL) AMINO] 5-CHLORO BENZAMIDE 37 g of methyl 2-allyloxy 4-[(1-H 4,5-dihydro 2-imidazolyl) amino] 5-chloro benzoate, 43 g of diethylaminoethylamine and 60 ml of methanol are placed in a 250 ml flask fitted with an agitator, a thermometer and a condenser. The reactants are heated under reflux (73° C.). The reactant suspension, which is initially thick, fluidifies and finally dissolves completely. After 96 hours of reaction the solution is cooled to 20° C. The crystals which form, are filtered, washed with methanol and oven-dried at 50° C.

weight=37 g 1st run.
Melting point=194° C.

The filtrate is evaporated under vacuum. 200 ml of water is added to the oily residue, which crystallizes. This second run is drained and washed with water. Weight=8 g 2nd run. The 8 g of product is dissolved in 35 ml of boiling ethanol and the product is allowed to recrystallize at room temperature. Thereafter, it is filtered and dried at 50° C.

Weight=3 g 3rd run.
Yield=37+3=40 g (85%).

This 3rd run product and the 1st run product are combined and recrystallized twice; first in 200 ml of ethanol and then in 165 ml of ethanol, with the intermediate product being dried.

Yield=28 g (60%).
Melting point=194° C.
Analysis of Product:

The product is 1% insoluble in water; the hydrochloride prepared for immediate use is 20% soluble in water.

The NMR spectrum is compatible with the structure of the expected product.

EXAMPLE XXXIV

N-[1-(1-CYCLOHEXENYLMETHYL) 2-PYRROLIDINYLMETHYL] 2-ALLYLOXY 4-[(1-H 4,5-DIHYDRO 2-IMIDAZOLYL) AMINO] 5-CHLORO BENZAMIDE 37 g of methyl 2-allyloxy 4-[(1-H 4,5-dihydro 2-imidazolyl amino) 5-chloro benzoate, 45 g of 1-(1-cyclohexenylmethyl) 2-aminomethyl pyrrolidine and 75 ml of methanol are placed in a 250 ml flask fitted with an agitator, a thermometer and a condenser. The reactants are heated for 96 hours under reflux, cooled to 20° C. and filtered. The filtrate is evaporated and the product is crystallized with 250 ml of water added. The solid is drained, washed with water and oven-dried at 50° C.

Yield=46 g (81%).
Melting point=194° C.

The product is recrystallized in 89 ml of (N)hydrochloric acid and 120 ml of water. It is filtered, and the filtrate is made alkaline with ammonia. The crystals formed are drained, washed with water and oven-dried at 50° C.

Yield=18 g (32%).
Melting point=189° C.

EXAMPLE XXXV

N-(ALLYL) 2-METHOXY 4-[(1-H 4,5-DIHYDRO 2-IMIDAZOLYL) AMINO] 5-CHLORO BENZAMIDE 85.05 g of methyl 2-methoxy 4-[(1-H 4,5-dihydro 2-imidazolyl) amino] 5-chloro benzoate, 200 ml of ethylene glycol and 51.3 g of allylamine are placed in a three-necked 1 liter bottle fitted with an agitator, a thermometer and a condenser, and heated for 2 hours at 70°-75° C. with agitation. 200 ml of water and 30 ml of 40% soda lye are then added and agitation is continued for one hour at 70°-75° C. The reaction mixture is cooled, drained, washed twice with 250 ml of water, then twice with 125 ml of acetone and dried at 70° C.

80.7 g is obtained (yield=87.1%).

Melting point: 224° C.

NMR: compatible, approximately 10% of ester present

Purification 79 g of the product is dissolved under reflux in 550 ml of dimethyl formamide containing 25% water. The solution is treated with black, filtered and crystallized overnight in a refrigerator. The product is drained, washed with acetone and dried.

This procedure yields 66 g of grey material, which is solubilized in 1320 ml of water and 30 ml of concentrated hydrochloric acid, treated with black and precipitated with 50 ml of ammonia. The precipitate is drained, washed and dried. It is still found to contain ester.

The product is agitated for 3 hours (at 80° C.) in 660 ml of water and 20 g of sodium hydroxide pellets. Then, it is filtered hot and washed twice with 300 ml of water. The resulting cake is dissolved in 3 liters of water and 30 ml of concentrated hydrochloric acid (pH 1), treated with black and precipitated with 50 ml of ammonia. The precipitate is left to stand overnight in a refrigerator, drained, washed with water and dried for 5 days at 60° C. under vacuum over $P_2O_5$.

44.6 g is obtained (purification yield=56.5%)

Analysis of Product:

MP (Kofler)=225° C.

$H_2O$<0.1%.

Titer=99.6%.

Cl=11.47% (calculated=11.48%).

The NMR and IR spectra are compatible with the structure proposed.

EXAMPLE XXXVI

N-(ISOPROPYL) 2-METHOXY 4-[(1-H 4,5-DIHYDRO 2-IMIDAZOLYL) AMINO] 5-CHLORO BENZAMIDE 85.05 g of methyl 2-methoxy 4-[(1-H 4,5-dihydro 2-imidazolyl) amino] 5-chloro benzoate, 200 ml of ethylene glycol and 53.1 g of isopropylamine are placed in a three-necked 1 liter bottle fitted with an agitator, a thermometer and a condenser and heated for 120 hours at 70°-75° C. with agitation. 200 ml of water and 30 ml of 40% soda lye are added and agitation is continued for a further hour at 70°-75° C. The mixture is cooled, drained, washed twice with 250 ml of water, then twice with 125 ml of acetone and dried at 70° C.

65.5 g of product is obtained (yield=70.3%).

Melting point=251° C.

NMR=compatible, ester just detectable.

Purification 64.2 g of the recovered product is dissolved hot (110° C.) in 275 ml of dimethyl formamide, treated with black, filtered and crystallized overnight in a refrigerator. The product is drained, washed with acetone and dried. 47.6 g of dried product is obtained (MP=251° C.)

The dried product is dissolved in 475 ml of water and 15 ml of concentrated hydrochloric acid, then treated with black, next, filtered and, finally, precipitated with 30 ml of 25% ammonia. The precipitate is left to stand in refrigerator for 2 hours, drained, washed with water and dried over $P_2O_5$, under vacuum at 60° C. for 4 days.

This procedure yields 41.8 g of product (purification yield: 65%).

Analysis of Product:

M P Kofler=249° C.

$H_2O$=0.1%.

Titer=100.0%.

Cl=11.39% (calculated=11.41%).

N=18.12% (calculated=18.03%).

The NMR and IR spectra are compatible with the proposed structure.

EXAMPLE XXXVII

N-(DIETHYLAMINO ETHYL) 2-METHOXY 4-[(4,5-DIHYDRO 1,3-THIAZOL 2-YL) AMINO] 5-CHLORO BENZAMIDE

Stage I: N-(5-METHOXY 4-METHOXYCARBONYL 2-CHLOROPHENYL) N'-(2-HYDROXY 1-ETHYL) THIOUREA 71 g of ethanol amine and 350 ml of methylene chloride are placed in 2 liter flask fitted with an agitator, a thermometer, a condenser and a bromine funnel. A filtered solution of 181 g of methyl 2-methoxy 4-isothiocyanato 5-chloro benzoate in 100 ml of methylene chloride is dripped in with the temperature of the contents of the flask cooled to 15°-20° C. The mixture is then agitated for 1.5 hours with the cold bath removed, and the precipitate which forms is drained. The precipitate is washed with a small quantity of methylene chloride and dried in an oven at 50° C.

Yield=188 g (84%).

M P=164°-170° C.

Analysis of Product:

The NMR spectrum is compatible with the structure of the expected product.

Stage II: METHYL 2-METHOXY 4-[(4,5-DIHYDRO 1,3-THIAZOL 2-YL) AMINO] 5-CHLORO BENZOATE 64 g of N-(5-methoxy 4-methoxycarbonyl 2-chlorophenyl) N'(2-hydroxy 1-ethyl) thiourea and 375 ml of methanol are placed in a one liter flask fitted with an agitator, a thermometer, a condenser and a bromine funnel. 20 ml of sulphuric acid (d=1.83) is dripped in the flask with the temperature of its contents reduced to 20° C.

The reaction mixture is heated for 4 hours under reflux, after which it is cooled and poured into 1000 ml of water and 300 g of ice. The entire mixture is brought to pH 9-10 with ammonia (d=0.90) and the precipitate which forms is drained, washed with water and dried in an oven at 50° C.

Yield=56 g (93%).

M P=189° C.

Analysis of Product:

The NMR spectrum is compatible with the structure of the expected product.

Stage III: N-(DIETHYLAMINO ETHYL) 2-METHOXY 4-[(4,5-DIHYDRO 1,3-THIAZOL 2-YL) AMINO] 5-CHLORO BENZAMIDE 45 g of methyl 2-methoxy 4-[(4,5-dihydro 1,3-thiazol 2-yl) amino] 5-chloro benzoate, 90 ml of methanol and 41.3 g of diethylaminoethylamine are placed in a 250 ml flask fitted with an agitator, a thermometer and a condenser. They are heated under reflux (70° C.) for two days and two nights, then the solution is cooled and the solvent evaporated under vacuum. 150 ml of water and 450 ml of ethyl acetate are added to the residue. The product crystallizes. The crystallized product is drained, washed with a small amount of ether and oven-dried at 50° C.

Yield=41.5 g (72%).
M P=about 112° C.

The product is recrystallized twice, with hot filtering in the presence of carbon black, first in 530 ml, then in 450 ml of ethyl acetate.

Yield=20 g (34%).
M P=162° C.

The product is compatible, but still has a small amount of solvent in its structure. It is dissolved in 180 ml of water and 12 ml of hydrochloric acid (d=1.18). The solution is filtered and ammonia (d=0.90) is added to the filtrate to bring it to pH 9-10. The resulting suspension is left to stand for 2 hours and the product is drained, washed with water and dried in an oven at 50° C.

Yield=15.5 g (27%).
M P=166° C.

Analysis of Product:
The NMR spectrum is compatible with the structure of the expected product.

EXAMPLE XXXVIII

N-(1-ETHYL 2-PYRROLIDINYLMETHYL) 2-METHOXY 4-[(4,5-DIHYDRO 1,3-THIAZOL 2-YL) AMINO] 5-CHLORO BENZAMIDE 45 g of methyl 2-methoxy 4-[(4,5-dihydro 1,3-thiazol 2-yl) amino] 5-chloro benzoate, 50 ml of 1-ethyl 2-aminomethyl pyrrolidine and 90 ml of methanol are placed in a 250 ml flask fitted with an agitator, a thermometer and a condenser. The reactants are agitated and heated under reflux (70° C.) for 3 days. The material gradually becomes soluble. It is cooled, the solvent is evaporated under vacuum and 300 ml of water is added to the pasty residue. The residue is extracted first with 400 ml, then with 100 ml of methylene chloride. The organic phase is washed 3 times with 200 ml of water then evaporated to dryness under vacuum. The residual paste is crystallized with 300 ml of ethyl acetate. The crystals are drained, washed with a small amount of solvent then dried in an oven at 50° C.

Yield=47.5 g (80%).
M P=144°-148° C.

The material is recrystallized in 200 ml of methanol. After standing in a refrigerator for 4 hours the crystals are drained, washed with water, then over-dried at 50° C.

Yield=31 g (52%).

The recovered solid is dissolved in 285 ml of water and 15 ml of HCl (d=1.18). The solution is filtered and the base is reprecipitated with 25 ml of ammonia (d=0.90). Large lumps form. These are drained, then crushed and dissolved moist in 100 ml of methanol. The mixture is heated under reflux until the solids are completely dissolved, then the product is allowed to recrystallize in a refrigerator for 1.5 hours. The crystals are drained, then washed with water and oven-dried at 50° C.

Yield=22 g (37%).
M P=147° C.

Analysis of Product:
The IR and NMR spectra are compatible with the structure of the expected product.

EXAMPLE XXXIX

N-(DIETHYLAMINO ETHYL) 2-METHOXY 4-[4,5-DIHYDRO 2-OXAZOLYL) AMINO] 5-CHLORO BENZAMIDE

Stage I: METHYL 2-METHOXY 4-[(4,5-DIHYDRO 2-OXAZOLYL) AMINO] 5-CHLORO BENZOATE 104 g of N-(2-chloro 4-methoxy carbonyl 5-methoxy phenyl) N'-(2-hydroxy 1-ethyl) thiourea, 846 ml of methanol and 80 g of methyl iodide are placed in a 4 liter flask fitted with an agitator, a thermometer, a condenser and a bromine funnel. The reactants are heated to 50°-55° C. for one hour, then cooled to 40° C. and a solution of 20 g of sodium in 320 ml of methanol is introduced in a thin stream. The mixture is then brought to reflux for 3.5 hours and left to stand overnight.

A solution of 40 g of ammonium chloride in 1000 ml of water and 40 ml of ammonia (d=0.90) is added to the mixture. The solution obtained is evaporated under vacuum to eliminate the methanol. 40 ml of ammonia (d=0.90) in 600 ml of water is also added and the resulting precipitate is drained. The precipitated crystals are dissolved in a solution of 30 ml of hydrochloric acid (d=1.18) in 300 ml of water, without any heating. The solution is filtered and the filtrate made alkaline with 40 ml of ammonia (d=0.90). The product is precipitated in the form of a gum-like material, which crystallizes. The white solid is drained, washed with water and oven-dried at 50° C.

Yield=68.5 g (74%).
MP=154° C.

Analysis of Product:
The NMR spectrum reveals the presence of a small amount of impurity.

Stage II: N-(DIETHYLAMINO ETHYL) 2-METHOXY 4-[(4,5-DIHYDRO 2-OXAZOLYL) AMINO] 5-CHLORO BENZAMIDE 34.2 g of 2-methoxy 4-[4,5-dihydro 2-oxazolyl) amino] 5-chloro benzamide, 70 ml of methanol and 33 g of diethylaminoethyl amine are placed in a 250 ml flask fitted with an agitator, a thermometer and a condenser.

The reactants are heated under reflux (approximately 70° C.) for about 31 hours. Complete solubilization is obtained after 2.5 hours under reflux. The material is cooled, the solvent is evaporated under vacuum, 100 ml of methylene chloride is added to dissolve the thick gum-like material, and the solution is washed with 50 ml of water three times. 150 ml of butyl acetate is added, the methylene chloride is evaporated under vacuum, 200 ml of butyl acetate is added, the mixture is heated to redissolve the solids and left to crystallize overnight at 20° C.

The crystals are drained and dried in an oven at 50° C.

Yield=25 g (57%).

The white solid is recrystallized in 100 ml of isopropanol. After standing for 3 hours in a refrigerator, the crystals are drained, washed with a small amount of solvent and dried in an oven at 50° C.

Yield: 22.5 g (51%).

The product is then dissolved in 150 ml of water and 173 ml of (N)hydrochloric acid, the solution is filtered and the filtrate is made alkaline with 20 ml of ammonia (d=0.90). The reaction mixture is left to crystallize for 2 days at 20° C., after which it is drained, washed with water and oven-dried at 50° C.

Yield=18 g (41%).

MP=137° C.

Analysis of Product:

The NMR and IR spectra are compatible with the structure of the expected product.

EXAMPLE XL

N-(1-CYCLOPROPYLMETHYL 2-PYRROLIDINYLMETHYL) 2-METHOXY 4-[(4,5-DIHYDRO 2-OXAZOLYL) AMINO] 5-CHLORO BENZAMIDE 42.7 g of methyl 2-methoxy 4-[(4,5-dihydro 2-oxazolyl) amino] 5-chloro benzoate, 65 ml of methanol and 46.2 g of 1-cyclopropylmethyl 2-aminomethyl pyrrolidine are placed in a 250 ml flask fitted with an agitator, a thermometer and a condenser. The suspension is heated under reflux (72° C.) for 26 hours. After 2.5 hours of heating the solid is totally dissolved. The material is cooled to 20° C., the solvent is evaporated under vacuum and the residual oil is crystallized with 125 ml of ethyl acetate. The material is left in a refrigerator for 4 hours, then the crystals are drained, washed 3 times with 30 ml of ethyl acetate and then oven-dried at 50° C.

Yield=32.3 g (53%).

MP=159° C.

The product is recrystallized in 80 ml of 95% ethanol then, without being dried, in 1200 ml of ethyl acetate. It is drained, washed with a small amount of ethyl acetate then oven-dried at 50° C.

Yield=20 g (33%).

MP=161° C.

Analysis of Product:

The NMR and IR spectra are compatible with the structure of the expected product.

The monohydrochloride prepared for immediate use is approximately 32% soluble in water.

The pharmacological properties of the compounds according to the invention has been investigated and their toxicology, studied. The chemical structure of these compounds suggests that they are similar to various known methoxybenzamide derivatives, which are known to exhibit antidopaminergic properties at different locations (of the CNS), which properties have led to the therapeutic applications such as antiemetic or psychotropic uses.

Biochemical and pharmacological tests of the compounds of this invention have shown that despite their structural similarity to known benzamides, the compounds of the invention;

did not become bound to the dopaminergic receptors during in vitro tests, whatever the type of $D_1$ or $D_2$ receptors;

did not cause any increase in prolacti in vivo, a typical biochemical effect of antidopaminergic drugs which work by blocking certain hypophysial dopamine receptors; did not counteract certain behavioural effects (emesis, climbing, hyperactivity, stereotyped movements etc.) induced in dogs, rats and mice by dopaminergic agonistic drugs, such as apomorphine and amphetamine, which agonists are currently used by pharmacologists to detect and measure the antidopaminergic effects of a drug;

did not produce any central depressive effect, except for certain cases at high doses. This effect may be toxic in origin, rather than neuroleptic;

did not induce catalepsy, as is a side-effect of neuroleptics.

The fact that there is no binding to dopaminergic receptors was demonstrated by the in vitro tests on rat striatum preparations. These tests which consisted of studying the displacement of specific ligands of dopamine receptors by compounds of the invention. The compound in Example I was found, for instance, to have an inhibiting concentration (50), I.C. 50, of over $10^{-4}M$ relative to $^3H$-spiperone, the ligand of $D_2$ receptors and no displacement of $^3H$-piflutixol, the ligand of $D_1$ receptors.

The fact that there is no increase in the prolactin in the blood after administration of the compounds of the invention was demonstrated in the male rat receiving the compound of Example I subcutaneously in a dose of 1 mg/kg. The test was carried out on eight rats and no increase in prolactin content was observed in the serum of these animals. The blood samples had been taken 10 and 30 minutes after administration of the compound, whereas the same dose of a reference antidopaminergic (Sulpiride) studied under the same conditions, multiplies the amount of basic prolactinaemia by a factor of about 10.

The fact that the compounds of the invention do not counteract the behavioral effects of apomorphine was demonstrated in dogs by the vomiting test (the effect was not significant up to 100 mcg/kg, given subcutaneously) and by the stereotypy tests in rats and climbing tests in mice. The compounds were not see to have any effect in any of these tests, even at very high doses such as 100 mg/kg.

The fact that the compounds have no cataleptigenic effect was seen in rats. After being given a dose, even a large one (100 mg/kg, administered subcutaneously) they were not able to remain in a set position.

Consequently the compounds of the invention cannot be regarded as antidopaminergic drugs acting as neuroleptics.

On the other hand, the inventive benzamides have the unexpected and important property of stimulating motor activity not only in rodents (rats and mice) but also in a primate: the marmoset. This property was demonstrated in rats located in individual cages fitted with photoelectric cells. Motor activity was measured according to how many times a light beam reaching the cells was interrupted. Measurements were taken between 8 p.m. and 10 p.m. and the results were expressed as a percentage of the value for the control rats. The animals appearance was also noted.

The graphs of FIGS. 1 to 15 indicate the strength of the activating effect of the compounds in various examples, at the dosage indicated, administered subcutaneously or intra accumbens.

FIGS. 1–10 represent graphically the motor activity in rats as a percentage of the value for control, as a function of a subcutaneously administered dose of the compounds of the varied Examples.

FIGS. 11–14 represent graphically the motor activity in rats as a percentage of the value for control, as a function of an intra-accumbens administered dose of the compounds of the various Examples.

It has also been demonstrated that the activating effect persists through chronic treatment.

Figure 1:
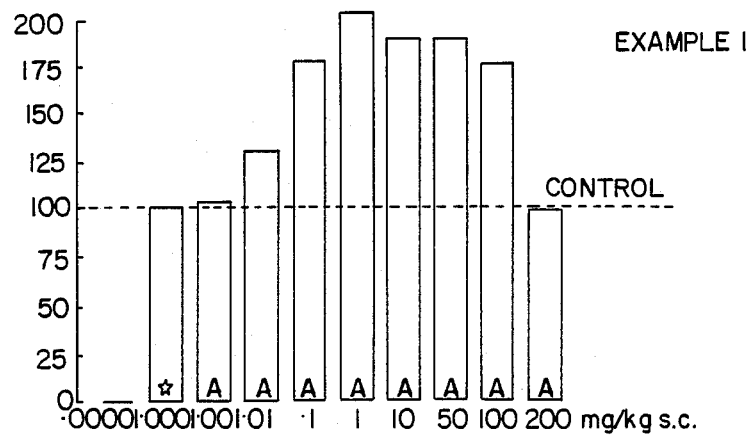
Figure 2:
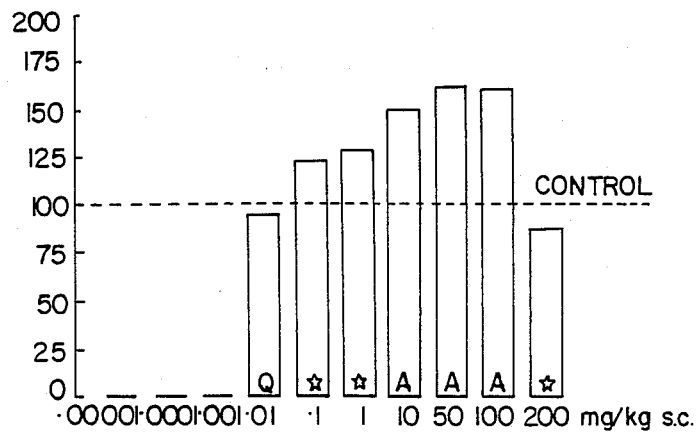
Figure 3:
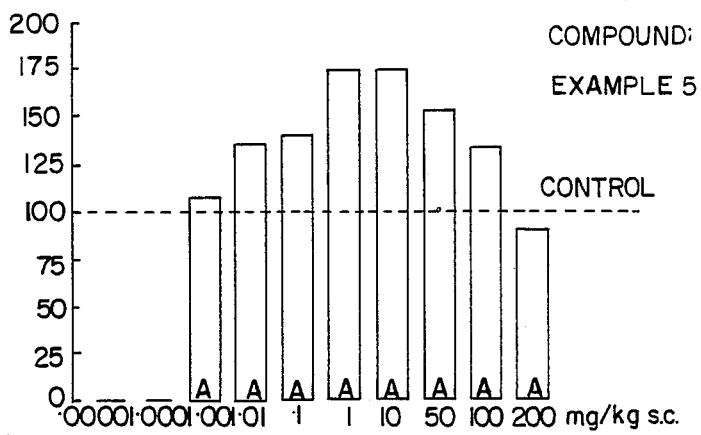
Figure 4:
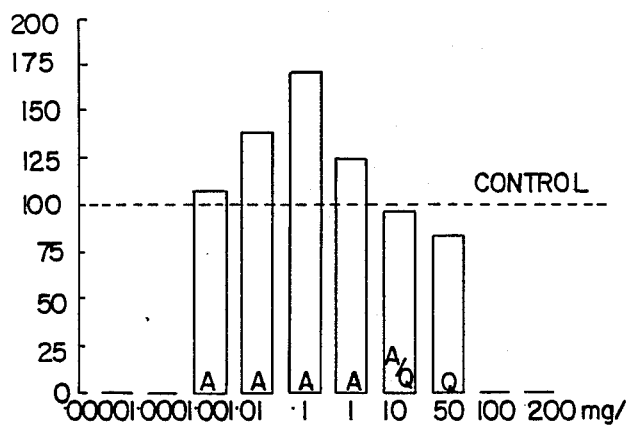
Figure 5:
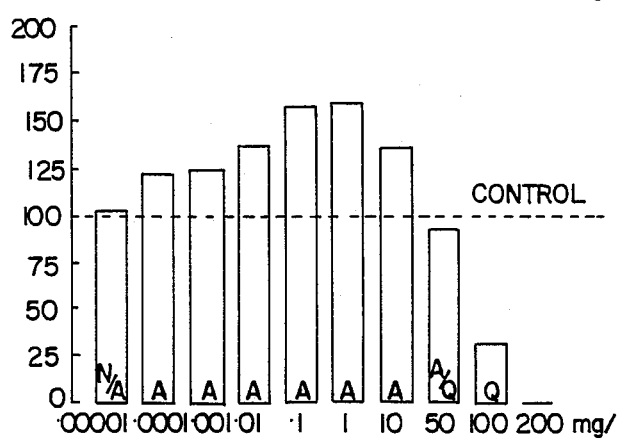
Figure 6:
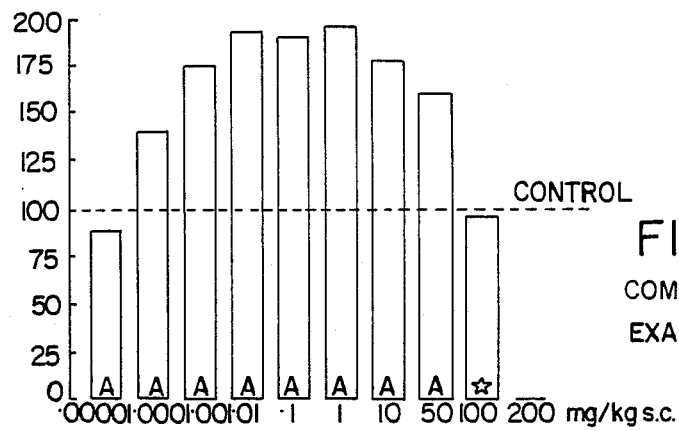
Figure 7:
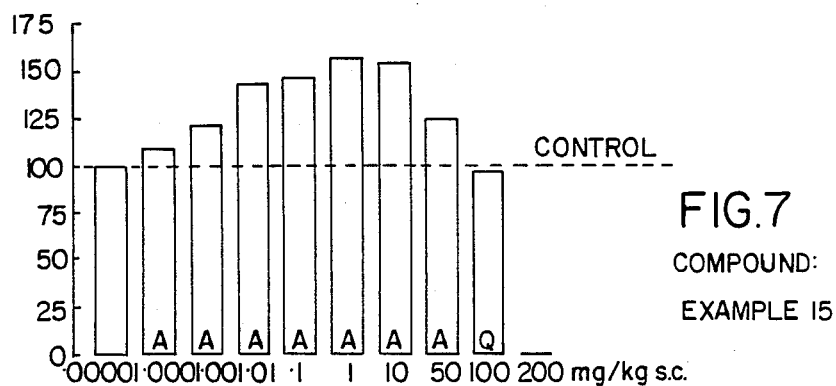
Figure 8:
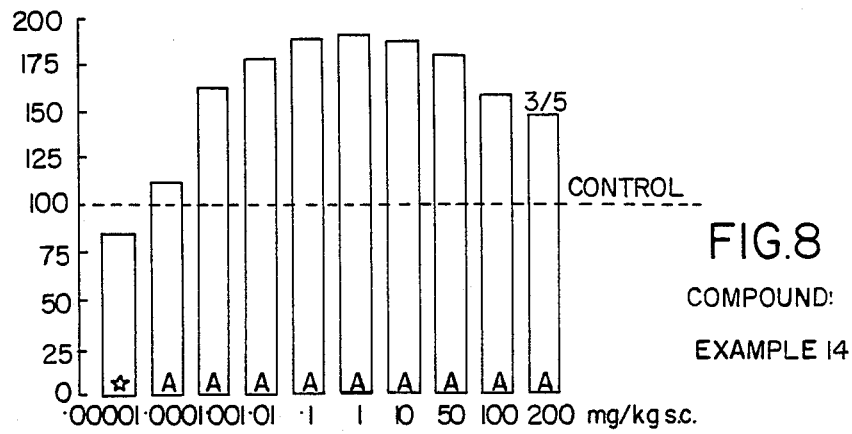
Figure 14:
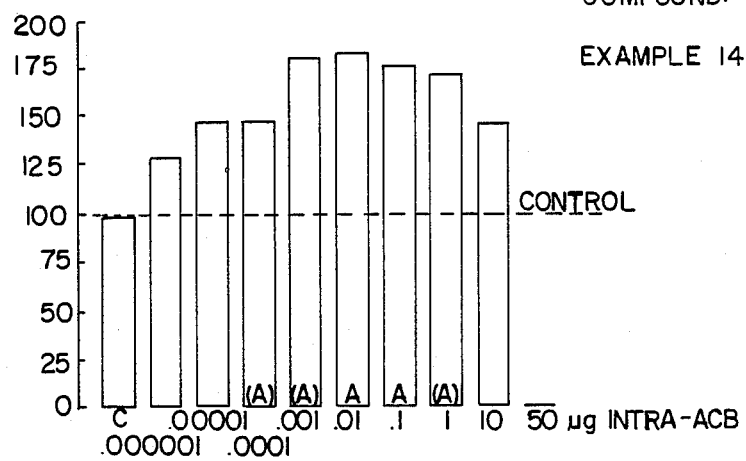
Figure 15:
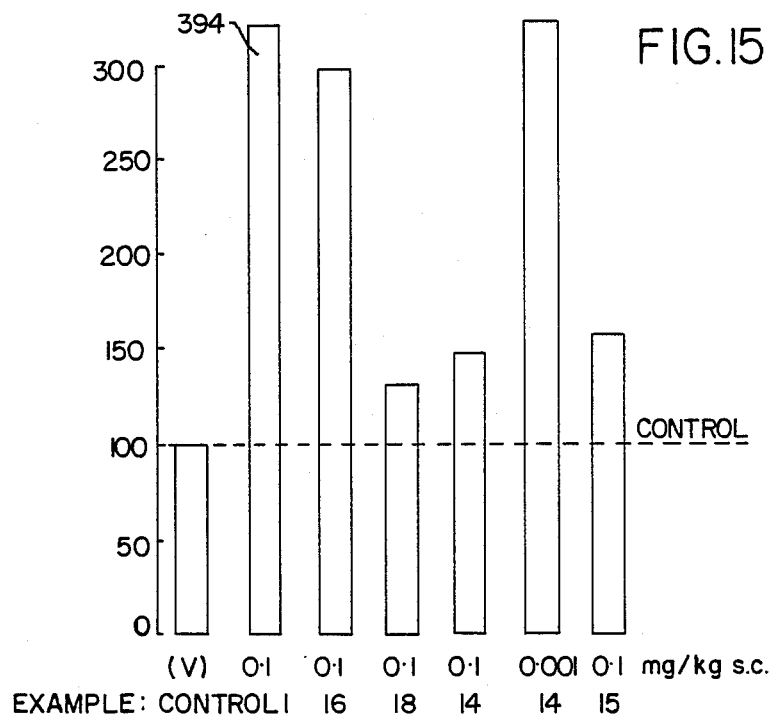
FIG. 15 represents graphically the motor activity in the marmoset as a percentage of the value for control, as a function of the subcutaneously administered dose of compounds of various Examples.
Figure 16:
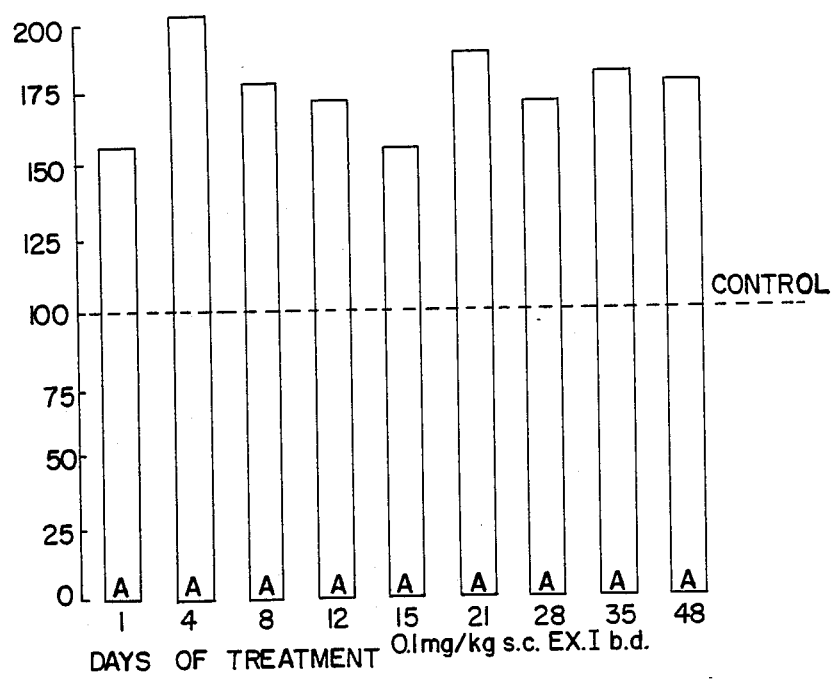

FIG. 16, for example, shows the effect of compound 1; 0.1 mg/kg administered subcutaneously to rats, daily with two injections per day for 48 days. Motor activity was recorded by photoelectric cells as in the single dose tests.

FIG. 16 represents graphically the motor activity in rats as a percentage of the value for control, as a function of the twice daily subcutaneously administered dosage of compound (1) over a 48 day period.

The activating effect of the inventive benzamide compounds has equally been demonstrated on the marmoset, placed in an individual two bar cage. The movements of the animal between the floor and the cage, the intermediate bar and the upper bar were recorded by an infra-red ray process.

In view of this activating property of the compounds of the invention, animal models of behavioural depression were used to investigate a possible antidepressive effect. For example, mice pre-treated with reserpine (5 mg/kg) intraperitoneally 18 hours before the test, or rats receiving reserpine in the nucleus accumbens 1 μg/24 h) were tested. The comound in Example 1, given subcutaneously in a dose of 0.1 mg/kg, counteracts motor depression and ptosis, and proves to be as active at that dose as 30 mg/kg of imipramine given intraperitoneally.

In the course of this pharmacological research a toxicological study of the most preferred compound was carried out. The following table shows the acute toxicity of the compound in Example I, giving the lethal dose 50 values for mice treated with different forms of administration.

| Form of administration | LD 50 (mg/kg) |
| --- | --- |
| i.v. | 12.8 –14.4 |
| s.c. | 52–54 |
| i.p. | 37.7–40.8 |
| per os | 165–180 |

This pharmacological profile of the compounds of the invention suggests that at lest the most active ones might have therapeutic applications in some forms of depression and/or psychomotor inhibition.

Pharmaceutical Composition

The compounds of the invention can be administered in any number of conventional forms such as capsules, tablets, pills, in granulated form or as an injectable solution. Many methods for compounding these preparations are well-known to the art. Substances which are inert relative to the compounds of the invention can be used in these preparations, such as lactose, magnesium, stearate, starch, talc, cellulose, levilite, alkali metal lauryl-sulphates, saccharose and other vehicles commonly employed in pharmaceutical preparations.

The compounds may be administered in doses of about 50–750 mg per day taken in 1 or more stages.

The examples which follow illustrate several pharmaceutical preparations, which can be made in a conventional manner from the compounds of the invention.

EXAMPLE XLI—tablets

| | |
| --- | --- |
| N—[(diethylamino)ethyl]2-methoxy 4[(1-H 4,5-dihydro 2-imidazolyl amino] 5-chloro benzamide | 100 mg |
| dried starch | 20 mg |
| lactose | 100 mg |
| methylcellulose 1500 cps | 1.5 mg |
| levilite | 10 mg |
| magnesium stearate | 4 mg |
| for 1 tablet. | |

EXAMPLE XLII—capsules

| | |
| --- | --- |
| N—[(1-ethyl 2-pyrrolidinyl)methyl] 2-methoxy 3,5-dibromo 4-[(1-H 4,5-dihydro 2-imidazolyl)amino] benzamide | 50 mg |
| microcrystalline cellulose | 50 mg |
| methylcellulose 1500 cps | 1 mg |
| magnesium stearate | 5 mg |
| talc | 2 mg |
| for 1 capsule. | |

EXAMPLE XLIII—injectable solution

| | |
| --- | --- |
| N—(diethylamino)ethyl 2-methoxy 4[(4,5-dihydro 1,3 thiazol 2-yl) amino] 5-chlorobenzamide | 40 mg |
| 1N hydrochloric acid | 0.1 ml |
| sodium chloride | 14 mg |
| for 2 ml. | |

EXAMPLE XLIV—injectable solution

| | |
| --- | --- |
| N—[1-1-cyclohexenylmethyl) 2-pyrrolidinyl methyl] 2-methoxy 4-[(1-H, 4,5-dihydro 2 imidazolyl) amino] | 100 mg |
| 1N hydrochloric acid | 0.250 ml |
| sodium chloride | 8 mg |
| for 2 ml. | |

To prepare the tablets, the selected compound is mixed with the starch and lactose by the method of succesive dilutions; the mixture is granulated with methylcellulose. The levilite, magnesium stearate and talc are added to the granules before proceeding with compression.

It is possible to replace the methylcellulose with any other appropriate granulating agent, such as ethylcellulose, polyvinylpyrrolidone or starch paste. The magnesium stearate may be replaced by stearic acid.

When preparing injectable solutions, it is possible to dissolve the compound of the invention in the following acids: hydrochloric or levulinic acid, gluconic acid, or glucoheptonic acid. The solution is prepared under sterile conditions and made isotonic with an alkali metal chloride such as sodium chloride, then preservatives are added. It is also possible to prepare the same solution without adding any preservatives: the ampoule is then filled under nitrogen and sterilized for ½ hour at 100° C.

What is claimed is:

1. Benzamide compounds of general formula (I)

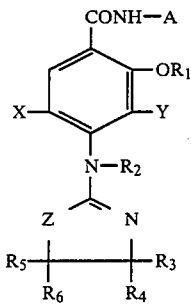

(I)

their optical isomers and their pharmacologically acceptable acid addition salts, wherein:

A is $C_1$–$C_6$ alkyl, $C_2$–$C_6$ alkenyl, diethylaminoethyl or a group of the formula:

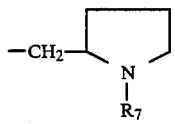

$R_7$ is hydrogen, $C_1$–$C_6$ alkyl, $C_2$–$C_6$ alkenyl, phenyl-substituted $C_1$–$C_6$ alkyl, $C_3$–$C_6$ cycloalkyl, $C_3$–$C_6$ cycloalkyl substituted $C_1$–$C_6$ alkyl, $C_4$–$C_6$ cycloalkenyl or $C_4$–$C_6$ cycloalkenyl substituted $C_1$–$C_6$ alkyl, $R_1$ and $R_2$ are each hydrogen, $C_1$–$C_6$ alkyl or $C_2$–$C_6$ alkenyl;

$R_3$, $R_4$, $R_5$ and $R_6$ are each hydrogen or a $C_1$–$C_6$ akyl;

X is halogen;

Y is hydrogen, or halogen;

Z is NH.

2. The benzamide of claim 1 having the formula (IA):

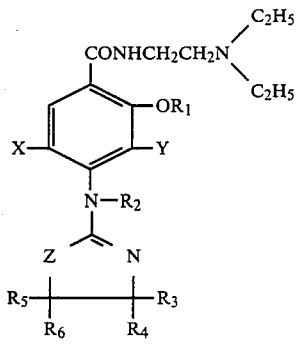

3. N-[2-(diethylamino) ethyl] 2-methoxy 4-[(1-H 4,5-dihydro 2-imidazolyl) amino] 5-chloro benzamide.

4. N-[2-(diethylamino) ethyl]2-methoxy 4-[N-ethyl, N-(1H 4,5-dihydro 2-imidazolyl) amino] 5-chloro benzamide.

5. N-[2-(diethylamino) ethyl] 2-methoxy 3,5-dichloro 4-[(1-H 4,5-dihydro 2-imidazolyl) amino] benzamide.

6. N-[2-(diethylamino) ethyl] 2-methoxy 4-[(1-H 4,5-dihydro 4-dimethyl 2-imidazolyl) amino] 5-chloro benzamide.

7. The benzamide of claim 1 having the formula (IB):

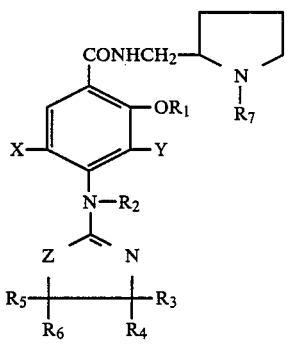

8. N-[(1-ethyl 2-pyrrolidinyl) methyl] 2-methoxy 3,5-dibromo 4-[(1-H 4,5-dihydro 2-imidazolyl) amino] benzamide.

9. N-1[(1-cyclohexenylmethyl 2-pyrrolidinyl) methyl] 2-methoxy 4-[(1-H 4,5-dihydro 2-imidazolyl amino] 5-chloro benzamide.

10. N-[(1-cyclopropylmethyl 2-pyrrolidinyl) methyl] 2-methoxy 4-[(1-H 4,5-dihydro 2-imidazolyl) amino] 5-chloro benzamide.

11. N(1-allyl 2-pyrrolidinyl methyl) 2-methoxy 4-[(1-H 4,5-dihydro 2-imidazolyl) amino] 5-chloro benzamide.

12. N-allyl 2-methoxy 4-[(1-H 4,5-dihydro 2-imidazolyl) amino] 5-chloro benzamide.

13. A pharmaceutical composition comprising a benzamide compound according to anyone of claims 1, 2 or 7 in amounts sufficient to impart antidepressive activity and a pharmaceutically acceptable carrier.

14. A pharmaceutical composition comprising a benzamide compound according to any one of claims 1, 2 or 7 in amounts sufficient to remove psychomotor inhibition and a pharmaceutically accetable carrier.

* * * * *

UNITED STATES PATENT AND TRADEMARK OFFICE
CERTIFICATE OF CORRECTION

PATENT NO. : 4,835,172
DATED : May 30, 1989
INVENTOR(S) : JACQUES ACHER, ET AL.       Page 1 of 9

It is certified that error appears in the above-identified patent and that said Letters Patent is hereby corrected as shown below:

Title page:

IN [75] INVENTORS

"Cachan;" should read --Cachan, of France;--
"Addingham," should read --Addingham, of England--
"all of France" should be deleted.

IN [56] REFERENCES CITED

U.S. PATENT DOCUMENTS, "Shon" should read --Shen et al.-- and "York" should read --York, Jr.--.

IN [57] ABSTRACT should read   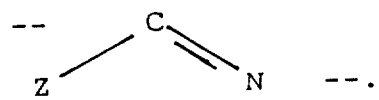  --.

COLUMN 1

Line 6, "relates" should read --relates to--.
Line 46, "atom," should read --atom.--.

COLUMN 2

Line 60, "N-[2(diethylamino)" should read --N-[2-(diethylamino)--.
Line 64, "N-[2(diethylamino)" should read --N-[2-(diethylamino)--.

UNITED STATES PATENT AND TRADEMARK OFFICE
CERTIFICATE OF CORRECTION

PATENT NO. : 4,835,172
DATED : May 30, 1989
INVENTOR(S) : JACQUES ACHER, ET AL.

Page 2 of 9

It is certified that error appears in the above-identified patent and that said Letters Patent is hereby corrected as shown below:

COLUMN 4

Line 62, "formulaa (VI)" should read --formula (VI)--.
Line 63, "werein" should read --wherein--.

COLUMN 5

Line 51, "haogen atom" should read --halogen atom--.

COLUMN 6

Line 29, "anc" should read --and--.
Line 67, "formula VIII" should read --formula (VIII)--.

COLUMN 7

Line 64, "haogen atom;" should read --halogen atom;--.

COLUMN 8

Line 21, "hyrazide" should read --hydrazide--.
Line 42, "hols" should read --hols,--.

COLUMN 10

Line 41, "of" should read --is--.

UNITED STATES PATENT AND TRADEMARK OFFICE
CERTIFICATE OF CORRECTION

PATENT NO. : 4,835,172
DATED : May 30, 1989
INVENTOR(S) : JACQUES ACHER, ET AL.

It is certified that error appears in the above-identified patent and that said Letters Patent is hereby corrected as shown below:

COLUMN 11

Line 51, "110 g (1,1 mole)" should read
        --110 g (1.1 mole)--.

COLUMN 12

Line 4, "Melting point=99." should read --Melting
        point=99°C.--.
    Line 19, "walls," should read --walls.--.

COLUMN 15

Line 4, "2-METHYOXY" should read --2-METHOXY--.
    Line 18, "cried," should read --dried,--.
    Line 36, "dried," should read --dried.--.
    Line 38, "treatment," should read --treatment.--.

COLUMN 16

Line 1, "are" should read --is--.
    Line 12, "2-methyoxy" should read --2-methoxy--.
    Line 43, "(purificaion" should read --(purification--.
    Line 50, "METHYL)]" should read --METHYL]--.

UNITED STATES PATENT AND TRADEMARK OFFICE
CERTIFICATE OF CORRECTION

PATENT NO. : 4,835,172

DATED : May 30, 1989

INVENTOR(S) : JACQUES ACHER, ET AL.

It is certified that error appears in the above-identified patent and that said Letters Patent is hereby corrected as shown below:

COLUMN 17

Line 14, "Melting point=120-122%" should read --Melting point=120-122°C.--.
    Line 26, "4-acetamido" should read --4-acetamino--.
    Line 34, "even" should read --oven--.
    Line 44, "(yield 78%)" should read --(yield 78%).--.
    Line 49, "4-acetamido" should read --4-acetamino--.

COLUMN 18

Line 1, "poured in" should read --poured in in--.
    Line 5, "5°C.," should read --5°C.--.

COLUMN 20

Line 46, "dried," should read --dried.--.
    Line 67, "dried," should read --dried.--.

COLUMN 21

Line 16, "99.5%," should read --99.5%.--.
    Line 25, "chloro benzoate," should read --5-chloro benzoate,--.
    Line 49, "5 CHLORO" should read --5-CHLORO--.

UNITED STATES PATENT AND TRADEMARK OFFICE
CERTIFICATE OF CORRECTION

PATENT NO. : 4,835,172
DATED : May 30, 1989
INVENTOR(S) : JACQUES ACHER, ET AL.          Page 5 of 9

It is certified that error appears in the above-identified patent and that said Letters Patent is hereby corrected as shown below:

COLUMN 23

Line 13, "(yield 86.1%)." should read --(yield: 86.1%).--.
Line 33, "250 m" should read --250 ml--.
Line 66, "procedure in" should read --procedure as in--.
Line 67, "2-methyl" should read --2-methoxy--.

COLUMN 24

Line 13, "Corrected: 18.0.3%;" should read --Corrected: 18.03%;--.
Line 21, "2-IMIDAZOLYL" should read --2-IMIDAZOLYL)--.
Line 36, "(Titer" should read --Titer--.
Line 44, "(Kofler) 217°C." should read --(Kofler): 217°C.--.
Line 45, "100°C. 0.01%." should read --100°C.: 0.01%.--.
Line 46, "Titer 98.8%." should read --Titer: 98.8%.--.
Line 47, "Br 19.61%" should read --Br: 19.61%--.
Line 48, "N 17.04%" should read --N: 17.04%--.
Line 65, "3 S ACTI CARBON" should read --3 S ACTI CARBONE--.

COLUMN 25

Line 2, "100°C. 0.33%." should read --100°C.: 0.33%.--.
Line 3, "(Kofler) 237°C." should read --(Kofler): 237°C.--.
Line 6, "Corrected: 18.0%;" should read --Corrected: 16.53%;--.

UNITED STATES PATENT AND TRADEMARK OFFICE
CERTIFICATE OF CORRECTION

PATENT NO. : 4,835,172
DATED : May 30, 1989
INVENTOR(S) : JACQUES ACHER, ET AL.    Page 6 of 9

It is certified that error appears in the above-identified patent and that said Letters Patent is hereby corrected as shown below:

COLUMN 25

Line 7, "18.50%." should read --16.50%.--.
    Line 16, "2-imidaolyl)" should read --2-imidazolyl)--.
    Line 32, "Br Found=18.4%;" should read
        --Br Found=18.47%;--.
    Line 40, "4,5DIHYDRO" should read --4,5-DIHYDRO-- and
        "2-IMIDAZOLYL" should read --2-IMIDAZOLYL)--.

COLUMN 26

Line 46, "4[(1-H" should read --4-[(1H)--.
    Line 64, "filered" should read --filtered--.
    Line 67, "166°C.," should read --165°C.,--.

COLUMN 27

Line 38, "compatible" should read --are compatible--.
    Line 54, "of" should be deleted.
    Line 57, "dripped" should read --dripped in--.

COLUMN 28

Line 20, "yield 77.4%." should read --yield 77.4%).--.

COLUMN 30

Line 23, "180°C.," should read --180°C.--.
    Line 42, "than" should read --then--.

UNITED STATES PATENT AND TRADEMARK OFFICE
CERTIFICATE OF CORRECTION

PATENT NO. : 4,835,172
DATED : May 30, 1989
INVENTOR(S) : JACQUES ACHER, ET AL.

It is certified that error appears in the above-identified patent and that said Letters Patent is hereby corrected as shown below:

COLUMN 31

Line 19, "N 16: 45%" should read --N16.45%--.

COLUMN 32

Line 57, "recrystallized isopropanol" should read --recrystallized with isopropanol--.
Line 65, "produce" should read --product--.

COLUMN 33

Line 1, "Corrected: 8.39" should read --Corrected: 8.39%--.
Line 9, "4[(1-H" should read --4-[(1-H--.

COLUMN 36

Line 17, "weight" should read --Weight--.
Line 50, "imidazolyl amino)" should read --imidazolyl) amino]--.

COLUMN 39

Line 62, "over-dried" should read --oven-dried--.

UNITED STATES PATENT AND TRADEMARK OFFICE
CERTIFICATE OF CORRECTION

PATENT NO. : 4,835,172
DATED : May 30, 1989
INVENTOR(S) : JACQUES ACHER, ET AL.

It is certified that error appears in the above-identified patent and that said Letters Patent is hereby corrected as shown below:

COLUMN 40

Line 15, "4-[4,5-DIHYDRO" should read --4-[(4,5-DIHYDRO--.
    Line 51, "4-[4,5-dihydro" should read --4-[(4,5-dihydro--.

COLUMN 41

Line 65, "prolacti" should read --prolactin--.
    Line 68, "receptors; did" should read --receptors; ¶ did--.

COLUMN 42

Line 14, "which" should be deleted.
    Line 39, "see" should read --seen--.
    Line 60, "animals" should read --animal's--.

COLUMN 43

Line 31, "1" should read --(1--.
    Line 32, "comound" should read --compound--.
    Line 43, Insert --EXAMPLE 1 COMPOUND-- as table heading.
    Line 51, "lest" should read --least--.
    Line 63, "magnesium," should read --magnesium--.

UNITED STATES PATENT AND TRADEMARK OFFICE
CERTIFICATE OF CORRECTION

PATENT NO. : 4,835,172
DATED : May 30, 1989
INVENTOR(S) : JACQUES ACHER, ET AL.

It is certified that error appears in the above-identified patent and that said Letters Patent is hereby corrected as shown below:

COLUMN 44   Line 8,

EXAMPLE XLI, "2-imidazolyl" should read --2-imidazolyl)--.
    Line 68, "formula (I)" should read --formula (I):--.

COLUMN 45

Line 54, "$C_1$-$C_6$ akyl;" should read --$C_1$-$C_6$ alkyl;--.
    Line 63, "formula (IA);" should read --formula (IA):--.

COLUMN 46

Line 19, "N-(1H" should read --N-(1-H--.
    Line 47, "2-imidazolyl" should read --2-imidazolyl)--.
    Line 58, "anyone" should read --any one--.
    Line 64, "accetable" should read --acceptable--.

Signed and Sealed this

Twelfth Day of November, 1991

Attest:

HARRY F. MANBECK, JR.

*Attesting Officer*  *Commissioner of Patents and Trademarks*